United States Patent [19]
Taniguchi et al.

[11] Patent Number: 5,863,918
[45] Date of Patent: Jan. 26, 1999

[54] NAPHTHALENE DERIVATIVES

[75] Inventors: Kiyoshi Taniguchi, Kobe; Masanobu Nagano, Kagoshima; Kouji Hattori, Takarazuka; Kazunori Tsubaki, Uji; Osamu Okitsu; Seiichiro Tabuchi, both of Nishinomiya, all of Japan

[73] Assignee: Fujisawa Pharmaceutical Co., Ltd., Osaka, Japan

[21] Appl. No.: 28,861

[22] Filed: Feb. 23, 1998

Related U.S. Application Data

[62] Division of Ser. No. 702,546, Oct. 10, 1996, Pat. No. 5,763,489.

[30] Foreign Application Priority Data

Mar. 10, 1994 [GB] United Kingdom .................... 9404734
Apr. 8, 1994 [GB] United Kingdom .................... 9407036

[51] Int. Cl.$^6$ .......................... A01N 43/58; C07D 237/00
[52] U.S. Cl. ........................................... 514/252; 544/239
[58] Field of Search ................. 514/252; 544/239

[56] References Cited

U.S. PATENT DOCUMENTS

| 5,132,307 | 7/1992 | Baumgarth et al. ..................... 514/247 |
| 5,344,836 | 9/1994 | Hamanaka et al. ...................... 514/332 |
| 5,596,009 | 1/1997 | Hamanaka et al. ...................... 514/357 |

FOREIGN PATENT DOCUMENTS 542203  5/1993  European Pat. Off. .

OTHER PUBLICATIONS

*Takemura et al*, Studies on Benzhydryl Derivatives. IV[1]) Synthesis and Anti–Inflammatory Activity of 2–O–(Diphenylacetyl)Salicylic Acids, Chem. Pharm. Bull. vol. 31, (1983), No. 8, pp. 2622–2638.

*Primary Examiner*—Mukund J. Shah
*Assistant Examiner*—Tamthom T. Ngo

*Attorney, Agent, or Firm*—Oblon, Spivak, McClelland, Maier & Neustadt, P.C.

[57] ABSTRACT

A compound or the formula:

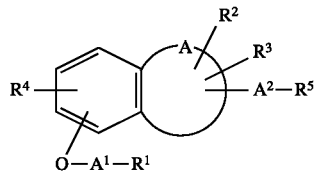

wherein $R^1$ is carboxy or protected carboxy,
$R^2$ is hydrogen, hydroxy or protected hydroxy,
$R^3$ is hydrogen, hydroxy, protected hydroxy, etc.,
$R^4$ is hydrogen or halogen,
$A^1$ is lower alkylene,
$A^2$ is bond or lower alkylene,
—$R^5$ is

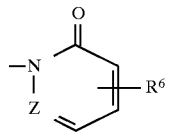

(in which $R^6$ is mono(or di or tri)aryl(lower)alkyl and Z is N or CH), etc., and

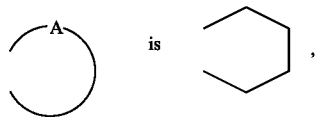

etc.,
and a pharmaceutically acceptable salt thereof which are useful as medicaments.

12 Claims, No Drawings

NAPHTHALENE DERIVATIVES

This is a division of Ser. No. 8/702,546, filed Oct. 10, 1996, now U.S. Pat. No. 5,763,489,

TECHNICAL FIELD

This invention relates to new naphthalene derivatives and pharmaceutically acceptable salts thereof which are useful as a medicament.

BACKGROUND ART

Some naphthalene derivatives have been known as described, for example, in EP 0542203A2.

DISCLOSURE OF INVENTION

This invention relates to new naphthalene derivatives. More particularly, this invention relates to new naphthalene derivatives and pharmaceutically acceptable salts thereof which have pharmacological activities such as an inhibitory activity on platelet aggregation, vasodilating activity, antihypertensive activity or the like and are prostaglandin $I_2$ agonists, to processes for their production, to a pharmaceutical composition containing the same and to a use thereof for manufacture of medicaments.

Accordingly, one object of this invention is to provide new and useful naphthalene derivatives and pharmaceutically acceptable salts thereof.

Another object of this invention is to provide processes for production of the naphthalene derivatives and salts thereof.

A further object of this invention is to provide a pharmaceutical composition containing, as an active ingredient, said naphthalene derivatives or pharmaceutically acceptable salts thereof.

Still further object of this invention is to provide use of the naphthalene derivatives and pharmaceutically acceptable salts thereof for manufacture of medicaments for the therapeutic and/or prophylactic treatment of arterial obstruction, cerebrovascular disease, hepatic cirrhosis, arteriosclerosis, ischemic heart disease, restenosls after percutaneous transluminal coronary angioplasty, hypertension or the like.

The naphthalene derivatives of this invention can be represented by the following formula (I)

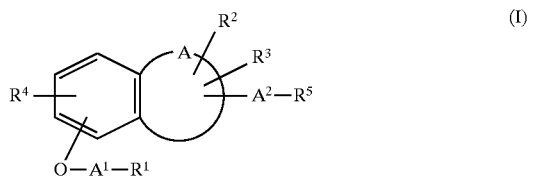

(I)

wherein $R^1$ is carboxy or protected carboxy, $R^2$ is hydrogen, hydroxy or protected hydroxy, $R^3$ is hydrogen, hydroxy, protected hydroxy, lower alkyl or halogen, $R^4$ is hydrogen or halogen, $A^1$ is lower alkylene, $A^2$ is bond or lower alkylene, —$R^5$ is

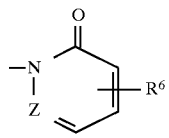

(in which $R^6$ is mono(or di or tri)aryl(lower)alkyl and Z is N or CH), or

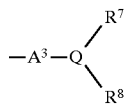

[in which —$A^3$— is

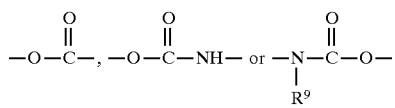

(wherein $R^9$ is hydrogen or lower alkyl), Q is N or CH, $R^7$ is aryl and $R^8$ is aryl], and

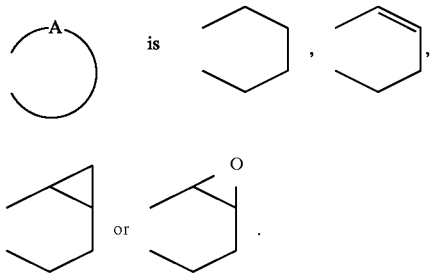

According to the present invention, the new naphthalene derivatives (I) can be prepared by the processes which are illustrated in the following scheme.

Process 1

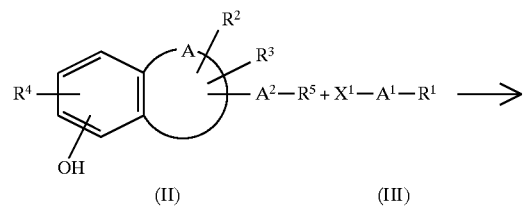

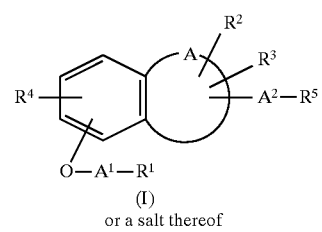

Process 2
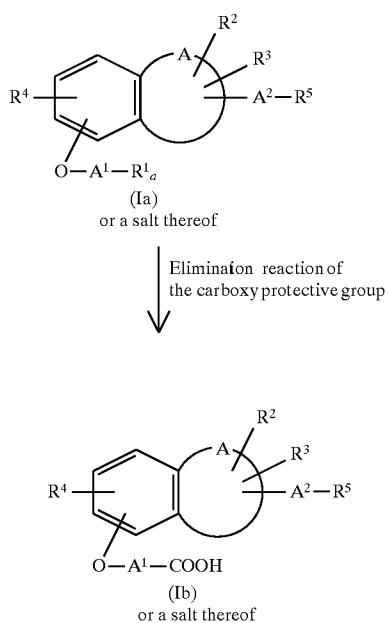
Process 3
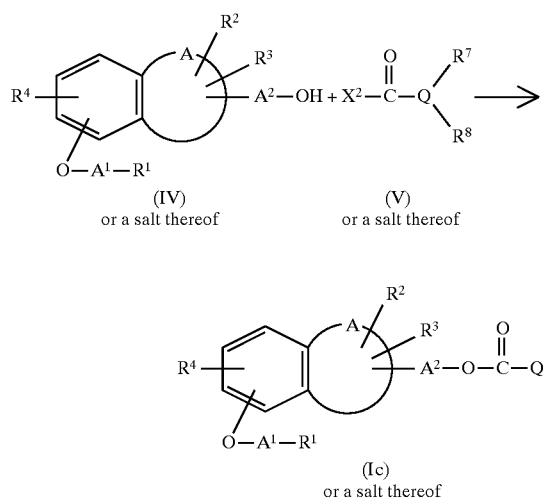
Process 4
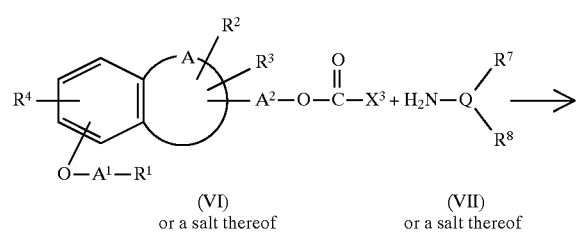
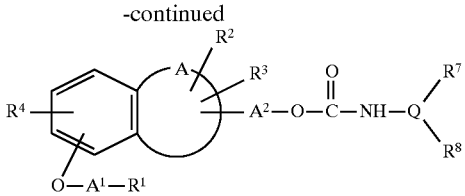
Process 5
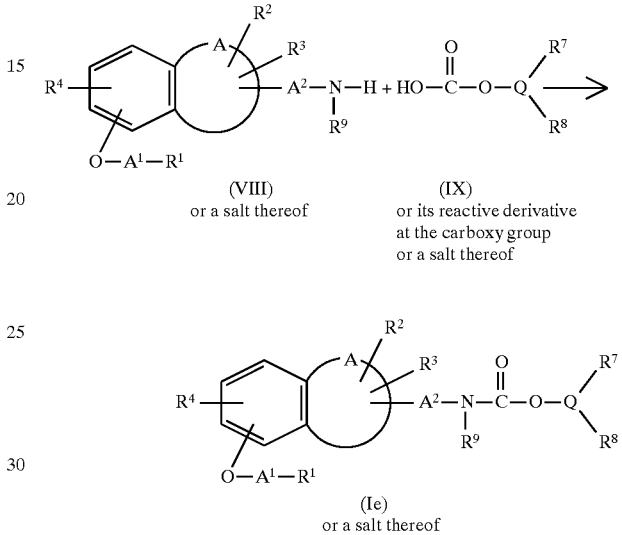
Process 6
wherein $R^1$, $R^2$, $R^3$, $R^4$, $R^5$, $R^7$, $R^8$, $R^9$, $A^1$, $A^2$, Q and
are each as defined above,
$X^1$ is acid residue,
$R_a^1$ is protected carboxy,
$X^2$ is halogen, $X^3$ is halogen, $X^4$ is halogen, and $R_a^9$ is lower alkyl.

Some of the starting compounds are novel and can be prepared by the following processes.

Process A

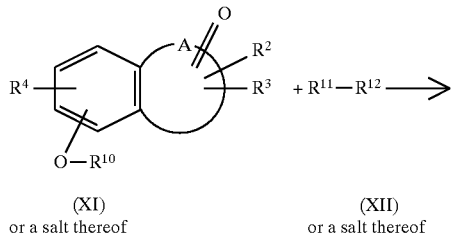

(XI)
or a salt thereof (XII)
or a salt thereof

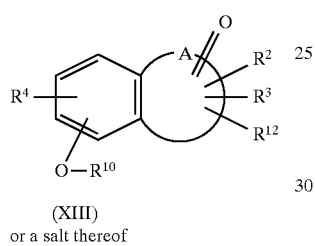

(XIII)
or a salt thereof

Process B

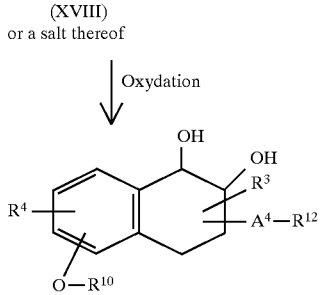

(XIV)
or a salt thereof

↓ Reduction

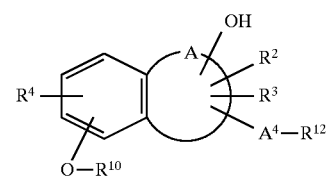

(XV)
or a salt thereof

Process C

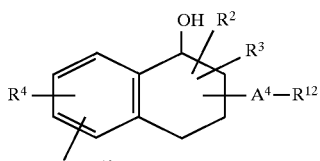

(XVI)
or a salt thereof

↓ Dehydration

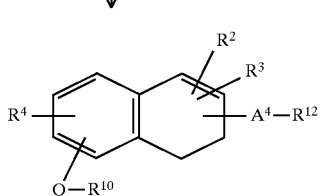

(XVII)
or a salt thereof

Process D

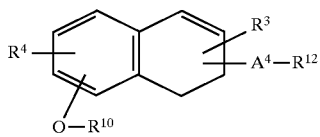

(XVIII)
or a salt thereof

↓ Oxydation

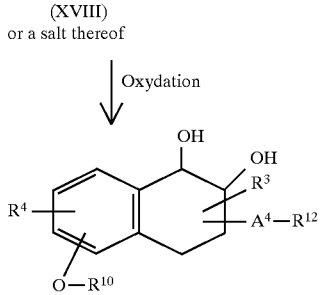

(XIX)
or a salt thereof

Process E

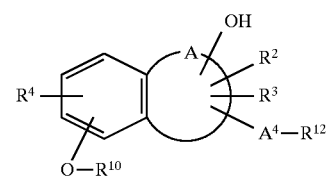

(XV)
or a salt thereof

↓ Halogenation

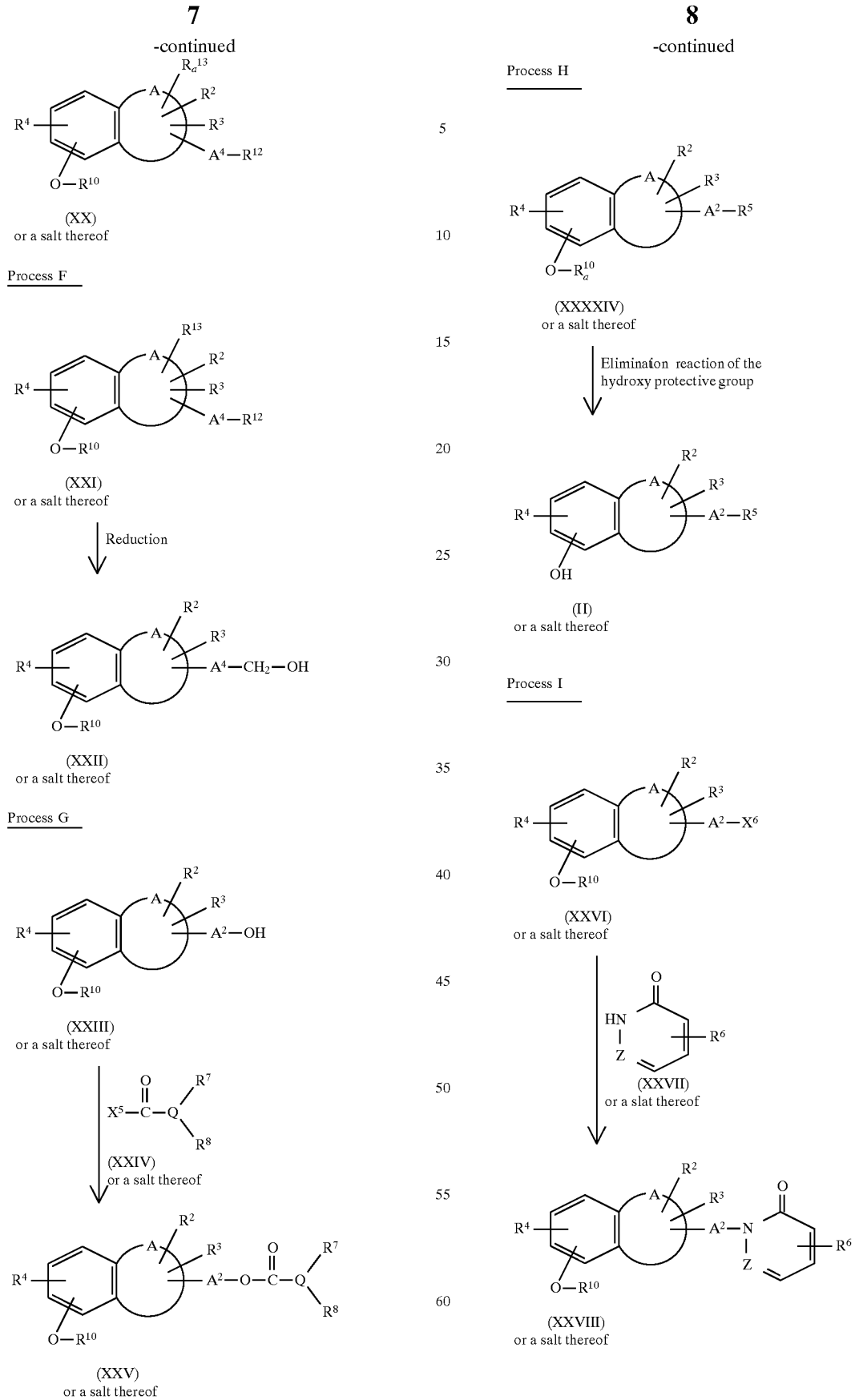

Process J

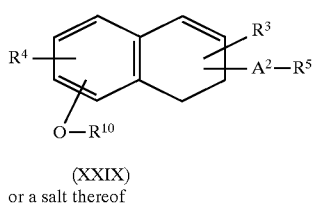

(XXIX)
or a salt thereof

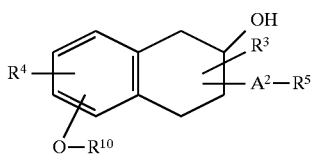

(XXX)
or a salt thereof

Process K

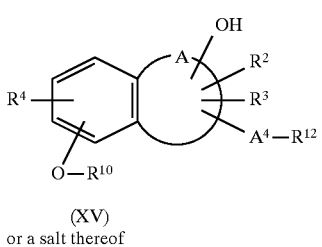

(XV)
or a salt thereof

| Reduction

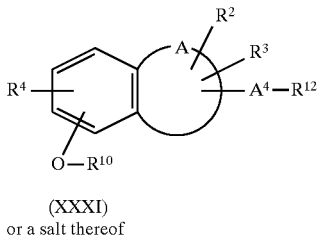

(XXXI)
or a salt thereof

Process L

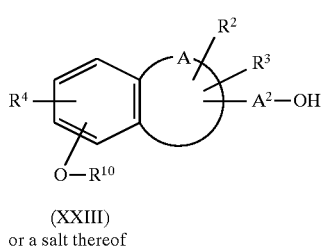

(XXIII)
or a salt thereof

| X$^7$—SO$_2$—R$^{14}$
(XXXII)
or a salt thereof

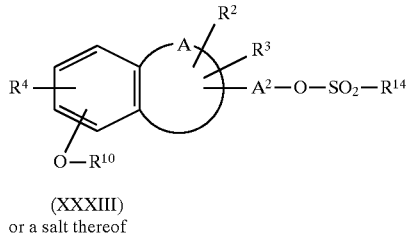

(XXXIII)
or a salt thereof

Process M

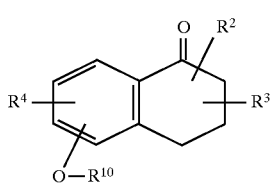

(XXXIV)
or a salt thereof $$R^{12}-CH_2-\overset{\overset{O}{\|}}{P}(OR^{15})_2$$
(XXXV)
or a salt thereof

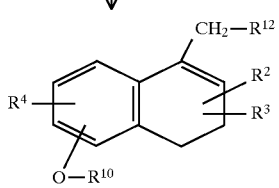

(XXXVI)
or a salt thereof

Process N

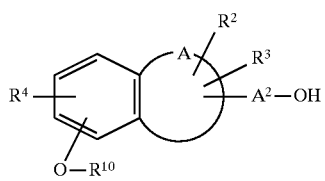

(XXIII)
or a salt thereof

| Halogenation

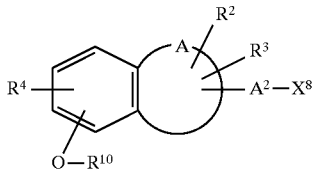

(XXXXV)
or a salt thereof

Process O

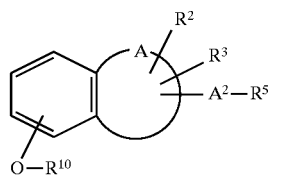

(XXXVII)
or a salt thereof

↓ Halogenation

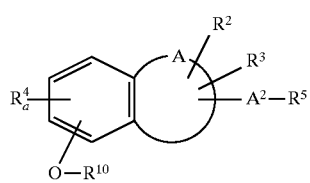

(XXXVIII)
or a salt thereof

Process P

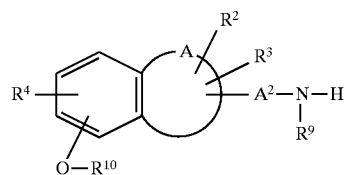

(XXXIX)
or a salt thereof $$\underset{\substack{\text{or its reactive derivative}\\\text{at the carboxy group}\\\text{or a salt thereof}}}{\text{HO}-\overset{\text{O}}{\underset{\|}{\text{C}}}-\text{O}-\text{Q}\genfrac{}{}{0pt}{}{R^7}{R^8}}$$

↓

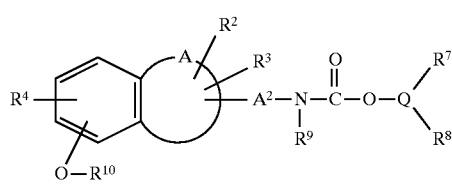

(XXXX)
or a salt thereof

Process Q

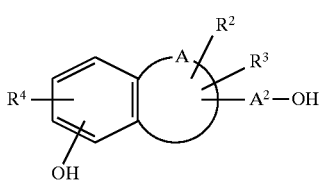

(XXXXI)
or a salt thereof

↓ $X^1-A^1-R^1$
(III)
or a salt thereof

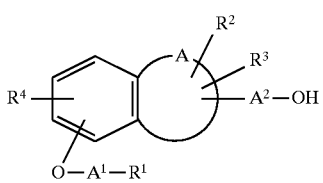

(IV)
or a salt thereof

Process R

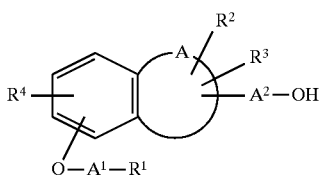

(IV)
or a salt thereof

↓ $X^3-\overset{\text{O}}{\underset{\|}{\text{C}}}-X^3$
(XXXXII)

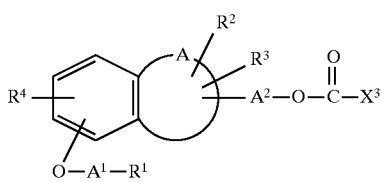

(VI)
or a salt thereof

Process S

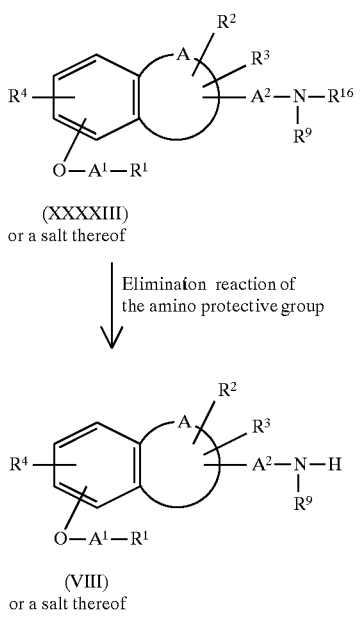

(XXXXIII)
or a salt thereof

↓ Elimination reaction of the amino protective group (VIII)
or a salt thereof wherein $R^1, R^2, R^3, R^4, R^5, R^6, R^7, R^8, R^9, A^1, A^2, Z, Q, X^1, X^3$ and

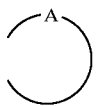

are each as defined above, $R^{10}$ is hydrogen or hydroxy protective group, $R^{11}$ is leaving group, $R^{12}$ is carboxy or protected carboxy, $A^4$ is bond or $C_1$–$C_5$ alkylene, $R_a{}^{13}$ is halogen, $R^{13}$ is hydrogen or halogen, $X^5$ is halogen, $R_a{}^{10}$ is hydroxy protective group, $X^6$ is acid residue, $X^7$ is halogen, $R^{14}$ is lower alkyl, or aryl which may have suitable substituent(s), $R^{15}$ is lower alkyl, $X^8$ is halogen, $R_a{}^4$ is halogen, and $R^{16}$ is amino protective group.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picokyine salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "aryl" and "aryl moiety" in the term "mono(or di or tri)aryl(lower)alkyl" may include phenyl, naphthyl and the like.

Suitable "lower alkylene" may include straight or branched one having 1 to 6 carbon atom(s), such as methylene, ethylene, trimethylene, tetramethylene, pentamethylene, hexamethylene or the like, preferably one having 1 to 3 carbon atom(s).

Suitable "$C_1$–$C_5$ alkylene" may include straight or branched one having 1 to 5 carbon atom(s), such as methylene, ethylene, trimethylene, tetramethylene, pentamethylene or the like.

Suitable "lower alkyl" and "lower alkyl moiety" in the term "mono(or di or tri)aryl(lower)alkyl may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1-(or 2)-pentanoyloxyethyl ester, etc.], lower alkylsulfonyl(lower) alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene (lower)alkyl ester, or (5-lower alkyl 2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)-phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Suitable "acid residue" may include halogen (e.g. chlorine, bromine, iodine, etc.), sulfonyloxy (e.g. methylsulfonyloxy, phenylsulfonyloxy, tolylsulfonyloxy, etc.), and the like.

Suitable "protected hydroxy" may include acyloxy and the like.

Suitable "acyl moiety" in the term "acyloxy" may include aliphatic acyl group and acyl group containing an aromatic or heterocyclic ring.

And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propcoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, Indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like.

Suitable "halogen" may include chlorine, bromine, iodine and fluorine.

Suitable "leaving group" may include lower alkoxy (e.g., methoxy, ethoxy, propoxy, isopropoxy, butoxy, etc.) and the like.

Suitable "substituent" in the term "aryl which may have suitable substituent(s)" may include lower alkyl as exemplified above, and the like.

Suitable "amino protective group" may include acyl as exemplified above, mono(or di or tri)aryl(lower)alkyl and the like.

Suitable "hydroxy protective group" may include lower alkyl as exemplified above, silyl which may have one to three suitable substituent(s), and the like.

Suitable "substituent" in the term "silyl which may have one to three suitable substituent(s)" may include lower alkyl as exemplified above, aryl as exemplified above, and the like.

Preferred embodiments of the object compound (I) are as follows:

$R^1$ is carboxy, or protected carboxy (more preferably esterified carboxy, most preferably lower alkoxycarbonyl), $R^2$ is hydrogen, hydroxy, or protected hydroxy (more preferably acyloxy), $R^3$ is hydrogen, hydroxy, protected hydroxy (more preferably acyloxy), lower alkyl or halogen, $R^4$ is hydrogen or halogen, $A^1$ is lower alkylene (more preferably $C_1$–$C_3$ alkylene, most preferably methylene), $A^2$ is bond, or lower alkylene (more preferably $C_1$–$C_3$ alkylene, most preferably methylene or ethylene), —$R^5$ is

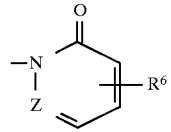

[in which $R^6$ is diaryl(lower)alkyl (more preferably diphenyl(lower)alkyl, most preferably diphenylmethyl), and Z is N or CH], or

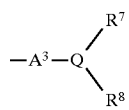

[in which —$A^3$— is

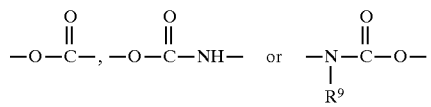

(wherein $R^9$ is hydrogen or lower alkyi), Q is N or CH, $R^7$ is aryl (more preferably phenyl), and $R^8$ is aryl (more preferably phenyl)], and

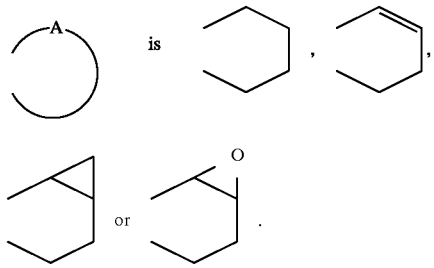

The processes for preparing the object and starting compounds of the present invention are explained in detail in the following.

Process 1

The compound (I) or a salt thereof can be prepared by reacting the compound (II) or a salt thereof with the compound (III) or a salt thereof.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of a base.

Suitable base may include the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkali metal bicarbonate (e.g. sodium bicarbonate, potassium bicarbonate, etc.), alkaline earth metal carbonate (e.g. magnesium carbonate, calcium carbonate, etc.) or the like, and the organic base such as tri(lower)alkylamine (e.g., trimethylamine, triethylamine, diisopropylethylamine, etc.), di(lower)alkylaniline (e.g. dimethylaniline, etc.), pyridine or the like.

Process 2

The compound (Ib) or a salt thereof can be prepared by subjecting the compound (Ia) or a salt thereof to elimination reaction of the carboxy protective group.

Suitable method of this reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picolinre, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, 1,2-dimethoxyethane, dioxane, a mixture thereof or any other solvent which does not adversely influence the reaction. A liquid base or acid can be also used as the solvent. The reaction temperature is not critical and the reaction is usually carried out under cooling to warming.

(ii) For reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process 3

The compound (Ic) or a salt thereof can be prepared by reacting the compound (IV) or a salt thereof with the compound (V) or a salt thereof.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of a base.

Suitable base can be referred to that of Process 1. A Liquid base can be also used as the solvent.

Process 4

The compound (Id) or a salt thereof can be prepared by reacting the compound (VI) or a salt thereof with the compound (VII) or a salt thereof.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of a base.

Suitable base can be referred to that of Process 1.

Process 5

The compound (Ie) or a salt thereof can be prepared by reacting the compound (VIII) or a salt thereof with the compound (IX) or its reactive derivative at the carboxy group or a salt thereof.

Suitable reactive derivative at the carboxy group of the compound (IX) may include an acid halide, an acid anhydride, an activated amide, an activated ester, and the like. The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl $[(CH_3)_2\overset{+}{N}=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-auinoiyl thioester, etc.), or an ester with a N-hydroxy compound (e.g. N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.), and the like. These reactive derivatives can optionally be selected from them according to the kind of the compound (IX) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (IX) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling to heating.

Process 6

The compound (Ig) or a salt thereof can be prepared by reacting the compound (If) or a salt thereof with the compound (X) or a salt thereof.

This reaction can be carried out in accordance with the method disclosed in the Example 20 described later or similar manners thereto.

Process A

The compound (XIII) or a salt thereof can be prepared by reacting the compound (XI) or a salt thereof with the compound (XII) or a salt thereof.

This reaction can be carried out in accordance with the method disclosed in the Preparation 31 described later or similar manners thereto.

Process B

The compound (XV) or a salt thereof can be prepared by subjecting the compound (XIV) or a salt thereof to reduction reaction.

This reaction can be carried out in accordance with the method disclosed in the Preparation 32 described later or similar manners thereto.

Process C

The compound (XVII) or a salt thereof can be prepared by subjecting the compound (XVI) or a salt thereof to dehydration reaction.

This reaction can be carried out in accordance with the method disclosed in the Preparation 33 described later or similar manners thereto.

Process D

The compound (XIX) or a salt thereof can be prepared by subjecting the compound (XVIII) or a salt thereof to oxidation reaction.

This reaction can be carried out in accordance with the methods disclosed in the Preparations 34 and 35 described later or similar manners thereto.

Process E

The compound (XX) or a salt thereof can be prepared by subjecting the compound (XV) or a salt thereof to halogenation reaction.

This reaction can be carried out in accordance with the method disclosed in the Preparation 40-(1) described later or similar manners thereto.

Process F

The compound (XXII) or a salt thereof can be prepared by subjecting the compound (XXI) or a salt thereof to reduction reaction.

This reaction can be carried out in accordance with the methods disclosed in the Preparations 1, 11, 13 and 40-(2) described later or similar manners thereto.

Process G

The compound (XXV) or a salt thereof can be prepared by reacting the compound (XXII) or a salt thereof with the compound (XXIV) or a salt thereof.

This reaction can be carried out in accordance with the methods disclosed in the Preparations 2 and 46 described later or similar manners thereto.

Process H

The compound (II) or a salt thereof can be prepared by subjecting the compound (XXXXIV) or a salt thereof to elimination reaction of the hydroxy protective group.

The reagent to be used in this reaction may include halotrialkylsilane (e.g., iodotrimethylsilane, etc.), alkali metal thioalkoxide (e.g., sodium thioethoxide, etc., alkali metal sulfide (e.g., sodium sulfide, etc.), alkali metal diphenylphosphide (e.g., lithium diphenylphosphide, etc.), aluminum halide (e.g., aluminum chloride, aluminum bromide, etc.), boron trihalide (e.g., boron trichloride, boron tribromlde, etc.), pyridine hydrochloride, alkylmagnesium halide (e.g., methylmagnesium iodide, etc.), lithium halide (e.g., lithium chloride, etc.), tetraalkylammonium halide (e.g., tetrabutylammonium fluoride, etc.), a combination of methionine and sulfonic acid (e.g., methanesulfonic acid, etc.), and the like.

The reaction is usually carried out in a conventional solvent such as water, alcohol, (e.g., methanol, ethanol, isopropyl alcohol, etc.), tetrahydrofuran, dioxane, dichloromethane, ethylene dichloride, chloroform, N,N-dimethylforamamide, N,N-dimethylacetamide, or any other organic solvent which does not adversely affect the reaction.

The reaction temperature is not critical and the reaction is usually carried out under cooling to heating.

Process I

The compound (XXVIII) or a salt thereof can be prepared by reacting the compound (XXVI) or a salt thereof with the compound (XXVII) or a salt thereof.

This reaction can be carried out in accordance with the method disclosed in the Preparations 8, 17 and 19 described later or similar manners thereto.

The compound (XXVII) or a salt thereof can be prepared in accordance with the method disclosed in the Preparation 7 described later or similar manners thereto.

Process J

The compound (XXX) or a salt thereof can be prepared from the compound (XXIX) or a salt thereof in accordance with the method disclosed in the Preparation 54 described later or similar manners thereto.

Process K

The compound (XXXI) or a salt thereof can be prepared by subjecting the compound (XV) or a salt thereof to reduction reaction.

This reduction can be carried out in a similar manner to that of the aforementioned Process 2, and therefore the reagents to be used and the reaction conditions (e.g., solvent, reaction temperature, etc.) can be referred to those of the Process 2.

Process L

The compound (XXXIII) or a salt thereof can be prepared by reacting the compound (XXIII) or a salt thereof with the compound (XXXII) or a salt thereof.

This reaction is usually carried out in a solvent such as acetonitrile, benzene, N,N-dimethylformamide, tetrahydrofuran, methylene chloride, ethylene chloride, pyridine, chloroform, diethyl ether or any other solvent which does not adversely affect the reaction.

The reaction temperature is not critical and the reaction is usually carried out under cooling to warming.

The reaction is usually carried out in the presence of a base.

Suitable base can be referred to that of Process 1.

Process M

The compound (XXXVI) or a salt thereof can be prepared by reacting the compound (XXXIV) or a salt thereof with the compound (XXXV) or a salt thereof.

This reaction can be carried out in accordance with the method disclosed in the Preparation 38 described later or similar manners thereto.

Process N

The compound (XXXXV) or a salt thereof can be prepared by subjecting the compound (XXIII) or a salt thereof to halogenation reaction.

This reaction can be carried out in accordance with the methods disclosed in the Preparations 14 and 15 described later or similar manners thereto.

Process O

The compound (XXXVIII) or a salt thereof can be prepared by subjecting the compound (XXXVII) or a salt thereof to halogenation reaction.

This reaction can be carried out in accordance with the method disclosed in the Preparation 21 described later or similar manners thereto.

Process P

The compound (XXXX) or a salt thereof can be prepared by reacting the compound (XXXIX) or a salt thereof with the compound (IX) or its reactive derivative at the carboxy group or a salt thereof.

This reaction can be carried out En a similar manner to that of the aforementioned Process 5, and therefore the reagents to be used and the reaction conditions (e.g. solvent, reaction temperature, etc.) can be referred to those of the Process 5.

Process Q

The compound (IV) or a salt thereof can be prepared by reacting the compound (XXXXI) or a salt thereof with the compound (III) or a salt thereof.

This reaction can be carried out in a similar manner to that of the aforementioned Process 1, and therefore the reagents to be used and the reaction conditions (e.g., solvent, reaction temperature, etc.) can be referred to those of the Process 1

Process R

The compound (VI) or a salt thereof can be prepared by reacting the compound (IV) or a salt thereof with the compound (XXXXII).

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to heating.

The reaction is usually carried out in the presence of a base.

Suitable base can be referred to that of Process 1.

Process S

The compound (VIII) or a salt thereof can be prepared by subjecting the compound (XXXXIII) or a salt thereof to elimination reaction of the amino protective group.

This reaction can be carried out in a similar manner to that of the aforementioned Process 2, and therefore the reagents to be used and the reaction conditions (e.g., solvent, reaction temperature, etc.) can be referred to those of the Process 2.

The object compound (I) of this invention and pharmaceutically acceptable salt thereof have pharmacological activities such as an inhibitory activity on platelet aggregation, vasodilating activity, antihypertensive activity or the like and are prostaglandin $I_2$ agonists, and therefore can be used for treating and/or preventing arterial obstruction (e.g., chronic arterial obstruction, etc.), cerebrovascular disease, gastric ulcer, hepatitis, hepatic insufficiency, hepatic cirrhosis, arteriosclerosis, ischemic heart disease, restenosis after percutaneous transluminal coronary angioplasty, hypertension, inflammation, heart failure, renal disease (e.g., renal failure, nephritis, etc.), diabetic complication (e.g., diabetic neuropathy, diabetic nephropathy, diabetic retinopathy, etc.), peripheral circulatory disturbance, and the like, and can be also used for protecting organs after transplantation.

In order to show the utility of the object compound (I), pharmacological data of the representative compounds thereof are shown in the following.

i) Inhibition of human platelet aggregation induced by ADP

[I] Test Compound:

(1) Sodium salt of [5-(carboxymethoxy)-2-hydroxy-1,2,3,4-tetrahydro-2-naphthyl]methyl N,N-diphenylcarbamate (2) 2-[(1,2,3,4-Tetrahydro-5-carboxymethoxy-2-naphthyl)methyl]-6-diphenylmethyl-3(2H)-pyridazinone

[III] Test Method:

Human blood was obtained from healthy volunteers and mixed with ⅒ volume of 3.8% sodium citrate, pH 7.4. The citrate blood was centrifuged at 150×g for 10 minutes and the platelet rich plasma (PRP) was removed. The remaining blood was centrifuged for a further 10 minutes at 1500×g to prepare the platelet poor plasma (PPP), which was used as a reference for platelet aggregation. Aggregation studies were carried out using HEMATRACER 801 (NBS, Japan), a 8 channel aggregometer. 25 $\mu$l of sample solution and 225 $\mu$l of PRP were mixed and stirred at 1000 rpm for 2 minutes at 37° C. Aggregation was induced by ADP solution at the final concentration of 2.5 $\mu$M.

[III] Test result:

| Test compound | Inhibition (%) |
|---|---|
| (1) (1.0 × 10⁻⁷ M) | 97 ± 1.2 |
| (2) (1.0 × 10⁻⁶ M) | 100 ± 0.4 | mean ± S.E.

ii) Effect on mean arterial blood pressure in conscious rats

[I] Test Compound:
Sodium salt of [5-(carboxymethoxy)-2-hydroxy-1,2,3,4-tetrahydro-2-naphthyl]methyl N,N-diphenylcarbamate

[II] Test Method:
Male Sprague-Dawley rats, aged 8–9 weeks, were anesthetized with ether. A polyethylene cannula filled with heparin solution was inserted into the femoral artery of the rats to measure mean blood pressure. Mean blood pressure was measured with a pressure transducer and recorded on a polygraph. The test compound dissolved in ethanol, polyethylene glycol and distilled water (1:1:1) was administered through a polyethylene cannula inserted into the femoral vein in a volume of 1 ml/kg. Intravenous hypotensive effect of the test compound was expressed as the maximal decrease (R max). Briefly, R max was expressed as maximal % change compared to mean blood pressure prior to the administration of the test compound.

[III] Test Result:

| Test compound | R max (%) |
|---|---|
| 10 mg/kg | 27.5 | iii) Receptor binding assay

[I] Test Compound:
Sodium salt of (2R)-[5-(carboxymethoxy)-2-hydroxy-1,2,3,4-tetrahydro-2-naphthyl]methyl N,N-diphenylcarbamate

[II] Test Method:
cDNA of human IP receptor was cloned and expressed in COS7 using pCDM8 vector in a similar manner to that described in the literatures [J. Biol. Chem., Vol. 269, No. 16, pp.12173–12178 (1994): Circulation, Vol. 90, No. 4, pp1643–1647 (1994) FEBS Letters 344 (1994) 74–78].

After transfection, cells which expressed human IP receptor were collected with ce 1 scraper at 4° C. and stored in −80° C.

The composition of assay buffer was as follows: 20 mM MES (pH 6.0), 10 mM $MgCl_2$, 1 mM EDTA, and 0.1 mM PMSF. Frozen cells were thawed and aliquots (4.5×10⁵ cells) were incubated for 60 minutes under shaking at 30° C. in plastic tubes in 100 μl of assay buffer with 10 nM of [³H]-iloprost in the presence or absence of the test compound (1×10⁻⁶M).

To determine the non-specific binding, iloprost at 10 μM was added. Each assay was preformed in duplicate. Reaction mixture was filtered through a Whatman GF/C glass filter to stop the reaction. After washing the filter with ice-cold assay buffer, the radioactivity of the filter was countered. Non-specific binding was subtracted from total binding to yield specific binding. The effect of the test compound was expressed as % inhibition of specific [³H]-iloprost binding.

[III] Test Result:
Inhibition (%): 96.5

The pharmaceutical composition of the present invention can be used in the form of a pharmaceutical preparation, for example, in solid, semisolid or liquid form (e.g. tablet, pellet, troche, capsule, suppository, cream, ointment, aerosol, powder, solution, emulsion, suspension etc.), which contains the object compound (I) or a pharmaceutically acceptable salt thereof as an active ingredient, suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylcellulose, polypropylpyrrolidone, gelatin, gum arabic, polyethyleneglyccl, sucrose, starch, etc.), disintegrator (e.g. starch, carboxymethyl cellulose, calcium salt of carboxymethyl cellulose, hydroxypropylstarch, sodium glycol-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

PREPARATION 1

A suspension of ethyl (5-methoxy-1,2,3,4-tetrahydro-1-naphthyl)acetate (1.02 g) and lithium aluminum hydride (0.20 g) in tetrahydrofuran (15 ml was stirred at 0° C. for 2.5 hours. The solution was poured into cold 1N-hydrochlorlc acid, then the resulting mixture was filtered through the celite, and extracted with ethyl acetate. The extract was washed with brine, dried over sodium sulfate, and evaporated in vacuo to afford 2-(5-methoxy- 1,2,3,4-tetrahydro-1-naphthyl)ethanol as a colorless oil (0.85 g).

NMR ($CDCl_3$, δ): 1.66–2.07 (7H, m), 2.49–2.76 (2H, m), 2.92–2.99 (1H, m), 3.77 (2H, t, J=6.8 Hz), 3.81 (3H, s), 6.67 (1H, d, J=8.0 Hz), 6.81 (1H, a, J=7.7 Hz), 7.11 (1H, dd, J=8.0, 7.7 Hz); (+) APCI MS m/z: 207 (M⁺+1)

PREPARATION 2

A mixture of (1,2,3,4-tetrahydro-5-methoxy-2-naphthyl) methanol (192 mg) and N,N-diphenylcarbamoyl chloride (348 mg) in pyridine (180 mg) was stirred at 100° C. for 2 hours, cooled to room temperature, and partitioned between ethyl acetate and 1N hydrochloric acid. The organic layer was washed successively with brine, aqueous sodium bicarbonate and brine, dried over magnesium sulfate, and evaporated in vacuo. The residue was triturated with diethyl ether to afford (1,2,3,4-tetrahydro-5-methoxy-2-naphthyl)methyl N,N-diphenylcarbamate (218 mg) as a pale purple powder.

mp: 143.5°–146° C.; IR (Nujol): 1710, 1260 cm⁻¹ NMR ($CDCl_3$, δ): 1.22–1.43 (1H, m), 1.8–2.05 (2H, m), 2.35–2.6

(2H, m), 2.65–2.9 (2H, m), 3.80 (3H, s), 4.06–4.23 (2H, m), 6.65 (1H, d, J=7.9 Hz), 6.65 (1H, d, J=7.9 Hz), 7.11 (1H, t, J=7.9 Hz), 7.16–7.38 (10H, m); (+) APCI MS m/z: 388 (M⁺+1)

PREPARATION 3

The following compound was obtained according to a similar manner to that of Preparation 2.

2-(5-Methoxy-1,2,3,4-tetrahydro-1-naphthyl)ethyl N,N-diphenylcarbamate mp: 97° C.;

IR (Nujol): 1710 cm⁻¹; NMR (CDCl₃, δ): 1.68–2.01 (6H, m), 2.46–2.74 (3H, m), 3.79 (3H, s), 4.26 (2H, t, J=6.4 Hz), 6.58 (1H, d, J=7.7 Hz), 6.64 (1H, d, J=8.0 Hz), 7.05 (1H, dd, J=8.0, 7.7 Hz), 7.16–7.38 (10H, m); (+) APCI MS m/z: 402 (M⁺+1)

PREPARATION 4

A suspension of (1,2,3,4-tetrahydro-5-methoxy-2-naphthyl)methyl N,N-diphenylcarbamate (1.93 g) and DL-methionine (7.43 g) in methanesulfonic acid (47.9 ml) was stirred at room temperature for 22 hours, then poured into ice water. The resulting mixture was extracted with ethyl acetate. The extract was washed successively with brine (twice), aqueous sodium bicarbonate and brine, dried over magnesium sulfate, and evaporated in vacuo. The residue was chromatographed (toluene-ethyl acetate) over silica gel to afford (1,2,3,4-tetrahydro-5-hydroxy-2-naphthyl)methyl N,N-diphenylcarbamate (82 mg) as yellow solids.

mp: 96°–98° C.; IR (Nujol): 3330, 1675, 1585 cm⁻¹; NMR (CDCl₃, δ): 1.25–1.47 (1H, m), 1.85–2.05 (2H, m), 2.42–2.59 (2H, m), 2.66–2.84 (2H, m), 4.07–4.23 (2H, m), 5.05 (1H, s), 6.58 (1H, d, J=7.7 Hz), 6.62 (1H, d, J=7.7 Hz), 6.96 (1H, t, J=7.7 Hz), 7.15–7.68 (10H, m); (+) APCI MS m/z: 374 (M⁺+1) Elemental Analysis Calcd. for C₂₄H₂₃NO₃: C 77.19, H 6.21, N 3.75; Found: C 77.31, H 6.29, N 3.67

PREPARATION 5

A suspension of 2-(5-methoxy-1,2,3,4-tetrahydro-1-naphthyl)ethyl N,N-diphenylcarbamate (0.93 g) and DL-methionine (3.50 g) in methanesulfonic acid (15 ml) was stirred at room temperature for 16 hours, then poured into ice water. The resulting mixture was extracted with ethyl acetate. The extract was washed successively with 5% hydrochloric acid and brine, dried over sodium sulfate, and evaporated in vacuo to afford crude 2-(5-hydroxy-1,2,3,4-tetrahydro-1-naphthyl)ethyl N,N-diphenylcarbamate (0.77 g).

EXAMPLE 1

A suspension of (1,2,3,4-tetrahydro-5-hydroxy-2-naphthyl)methyl N,N-diphenylcarbamate (67 mg), ethyl bromoacetate (33 mg) and potassium carbonate (37 mg) in N,N-dimethylformamide (1.0 ml) was stirred at room temperature for 5.5 hours and then extracted with ethyl acetate. The extract was washed with water and brine (twice), dried over magnesium sulfate, and evaporated in vacuo. The residue was chromatographed (toluene-ethyl acetate) over silica gel to afford [5-(ethoxycarbonylmethoxy)-1,2,3,4-tetrahydro-2-naphthyl]methyl N,N-diphenylcarbamate (61 mg) as an oil.

IR (Film): 1755, 1710, 1585, 1200 cm⁻¹ (+) APCI MS m/z: 460 (M⁺+1)

EXAMPLE 2

The following compound was obtained according to a similar manner to that of Example 1.

2-[5-(Ethoxycarbonylmethoxy)-1,2,3,4-tetrahydro-1-naphthyl]ethyl N,N-diphenylcarbamate IR (Film): 1760–1700 (broad) cm⁻¹; NMR (CDCl₃, δ): 1.29 (3H, t, J=7.1 Hz), 1.57–2.30 (6H, m), 2.48–2.76 (3H, m), 4.18–4.31 (4H, m), 4.60 (2H, s), 6.50 (1H, d, J=8.0 Hz), 6.61 (1H, d, J=7.7 Hz), 7.01 (1H, dd, J=8.0, 7.7 Hz), 7.05–7.38 (10H, m); (+) APCI MS m/z: 474 (M⁺+1)

EXAMPLE 3

A solution of [5-(ethoxycarbonylmechoxy)-1,2,3,4-tetrahydro-2-naphthyl]methyl M, N-diphenylcarbamate (59 mg) and 1N sodium hydroxide solution (0.15 ml) in ethanol (1.5 ml) was stirred at room temperature for 1 hour and neutralized with 1N hydrochloric acid (0.15 ml), then extracted with ethyl acetate. The extract was washed with brine, dried over magnesium sulfate, and evaporated in vacuo. The residue was powdered from n-hexane to afford [5-(carboxymethoxy)-1-,2,3,4-tetrahydro-2-naphthyl] methyl N,N-diphenylcarbamate (47 mg) as a colorless powder.

mp: 137°–141.5° C.; IR (Nujol): 1740, 1705, 1580, 1250 cm⁻¹; NMR (DMSO-d₆, δ): 1.2–1.35 (1H, m), 1.75–2.0 (2H, m), 2.27–2.83 (4H, m), 4.06 (2H, br d, J=5.8 Hz), 4.64 (2H, s), 6.59 (1H, d, J=7.8 Hz), 6.63 (1H, d, J=7.8 Hz), 7.01 (1H, t, J=7.8 Hz), 7.23–7.43 (10H, m), 12.95 (1H, br s); (+) APC MS m/z: 432 (M⁺+1)

EXAMPLE 4

A solution of 2-[5-(ethoxycarbonylmethoxy)-1,2,3,4-tetrahydro-1-naphthyl]ethyl N,N-diphenylcarbamate (0.83 g) and 1N sodium hydroxide solution (2.1 ml) in dioxane (5 ml) was stirred at room temperature for 30 minutes and washed with ether. The resulting aqueous layer was acidified with 10% hydrochloric acid and extracted with ethyl acetate. The extract was washed with brine, dried over sodium sulfate, and evaporated in vacuo. The residue was powdered from 2-propanol to afford 2-[5-(carboxymethoxy)-1,2,3,4-tetrahydro-1-naphthyl]ethyl N,N-diphenylcarbamate 10.46 g) as a colorless cowder.

mp: 145° C.; IR (Nujol): 1730, 2695 cm⁻¹; NMR (DMSO-d₆, δ): 1.60–1.91 (6H, m), 2.42–2.60 (3H, m), 3.57 (1H, broad), 4.15 (2H, t, J=6.2 Hz), 4.61 (2H, s), 6.54 (1H, d, J=7.7 Hz), 6.57 (1H, d, J=8.1 Hz), 6.99 ( H, dd, J=8.1, 7.7 Hz), 7.20–7.41 (10H, m); (+) APCI MS m/z: 446 (M⁺+1)

EXAMPLE 5

A solution of 2-[5-(carboxymethoxy)-1,2,3,4-tetrahydro-1-naphthyi]ethyl N,N-diphenylcarbamate (0.12 g) and 1N-sodium hydroxide solution (0.265 ml) in ethanol was evaporated in vacuo. The residue was powdered from ethanol to afford sodium salt of 2-[5-(carboxymethoxy)-1,2,3,4-tetrahydro-1-naphthyl]ethyl N,N-diphenylcarbamate (0.11 g) as a colorless powder.

mp: 200°–215° C.; IR (Nujol): 1700, 1610 cm⁻¹; NMR (CD₃OD, δ): 1.67–2.01 (6H, m), 2.57–2.85 (3H, m), 4.18–4.26 (2H, m), 4.35 (2H, s), 6.49 (1H, d, J=7.7 Hz), 6.56 (1H, d, J=8.1 Hz), 6.94 (1H, dd, J=8.1, 7.7 Hz), 7.20–7.40 (10H, m); FAB MS m/z: 468 (M⁺)

EXAMPLE 6

To a solution of [5-(ethoxycarbonylmethoxy)-2-hydroxy-1,2,3,4-tetrahydro-2-naphthyl]methyl N,N- diphenylcarbamate (570 mg) in ethanol (20 ml) was added 1N-sodium hydroxide solution (1.2 ml). After stirring for 4 hours at room temperature, the solvent was removed in vacuo to give sodium salt of [J- (carboxymethoxy)-2-hydroxy-1,2,3,4-tetrahydro-2-naphthyl]nethyl N,N-diphenylcarbamate (500 mg).

IR (Nujol): 3300–3400, 1700, 1580 cm$^{-1}$; NMR (D$_2$O, δ): 1.2–1.6 (2H, m), 2.1–2.6 (4H, m) 3.72 (1H, d, J=11.0 Hz), 3.85 (1H, d, J=11.0 Hz), 4.13 (2H, s), 6.29 (2H, m), 6.4–7.0 (12H, m); FAB MS m/z: 470 (M$^+$+1)

PREPARATION 6

To a solution of (5-methoxy-1,2,3,4-tetrahydro-2-naphthyl)methanol (1.00 g) in dry pyridine (10 ml) was added p-toluenesulfonyl chloride (1.15 g) under ice bath cooling. The mixture was stirred for 1 day at room temperature and partitioned between ethyl acetate and water. The organic layer was separated, washed with water (twice), 1N hydrochloric acid and brine, dried over magnesium sulfate, and evaporated in vacuo. The residue was purified by silica gel column chromatography (n-hexane:ethyl acetate =10:1) to give (5-methoxy-1,2,3,4-tetrahydro-2-naphthyi)methyl p-toluenesulfonate (1.70 g) as a white powder.

mp: 81°–82° C.; IR (Nujol): 1590, 1370, 1260, 1180, 790, 770, 720 cm$^{-1}$; MASS (+APCI): 347 (M$^+$+1) NMR (CDCl$_3$, δ): 1.10–1.50 (1H, m), 1.80–2.20 (2H, m), 2.20–2.60 (2H, m), 2.45 (3H, s), 2.60–2.95 (2H, m), 3.79 (3H, s), 3.99 (2H, d, J=6.6 Hz), 6.64 (1H, d, J=7.9 Hz), 6.64 (1H, d, J=7.9 Hz), 7.07 (1H, dd, J=7.9 Hz, 7.9 Hz), 7.34 (2H, d, J=8.2 Hz), 7.79 (2H, d, J=8.2 Hz)

PREPARATION 7

A solution of 1,1-diphenylacetone (25 g) and glyoxylic acId monohydrate (41.6 g) in 1,2-dimethoxyethane (75 ml) was refluxed for 3 days. The solution was partitioned between ethyl acetate and water. The organic layer was washed with water (twice) and evaporated in vacuo. The residue was oartitioned between ethyl acetate and ammonia solution (200 ml) and the aqueous layer was separated. To the aqueous layer was added hydrazine hydrate (22.6 g) and the mixture was stirred for 2 hours at 100° C. After being cooled, the reaction mixture was extracted with ethyl acetate. The extract was dried over magnesium sulfate and evaporated in vacuo. The residue was recrystallized from ethyl acetate to give 6-diphenylmethyl-3(2H)-pyridazinone (6.26 g) as a white powder.

mp: 161°–162° C.; IR (Nujol): 3300–2800, 1660, 1600, 760, 740, 700 cm$^{-1}$; NMR (CDCl$_3$, δ): 5.44 (1H, s), 6.88 (1H, d, J=9.8 Hz), 7.10–7.40 (11H, m), 11.29 (1H, br s) MASS (+APCI): 263 (M$^+$+1); Elemental Analysis Calcd. for C$_{17}$H$_{14}$N$_2$O: C 77.84, H 5.38, N 10.68; Found : C 77.76, H 5.39, N 10.66

PREPARATION 8

A suspension of 6-diphenylmethyl-3(2H)-pyridazinone (0.58 g) and sodium hydride (60%, 110 mg) in dry N,N-dimethylformamide (7 ml) was stirred at 0° C. for 30 minutes. A solution of (5-methoxy-1,2,3,4-tetrahydro-2-naphthyl)methyl p-toluenesulfonate (0.77 g) in dry N,N-dimethylformamide (5 ml) was added dropwise to the suspension at room temperature. The mixture was stirred for 6 hours and poured into ice-1N hydrochloric acid and extracted with ethyl acetate. The extract was separated, washed with water (twice) and brine, dried over magnesium sulfate, and evaporated in vacuo. The residue was purified by silica gel column chromatography (n-hexane: ethyl acetate =5:1~3:1) to give 2-[(1,2,3,4-tetrahydro-5-methoxy-2-naphthyl)methyl]-6-diphenylmethyl-3(2H)-pyridazinone (0.61 g) as a pale yellow oil.

IR (Film): 1660, 1590, 770, 730, 700 cm$^{-1}$; NMR CDCl$_3$, δ): 1.35–1.55 (1H, m), 1.80–2.00 (1H, m), 2.25–3.00 (5H, m), 3.80 (3H, s), 4.05–4.25 (2H, m), 5.45 (1H, s), 6.61 (1H, d, J=6.9 Hz), 6.64 (1H, d, J=6.9 Hz), 6.87 (1H, d, J=9.5 Hz), 7.00–7.35 (12H, m); MASS (+APCI): 437 (M$^+$+1)

PREPARATION 9

To a solution of 2-[(1,2,3,4-tetrahydro-5-methoxy-2-naphthyl)methyl]-6-diphenylmethyl-3(2H)-pyridazinone (0.60 g) in dry dichloromethane (5 ml) was added drocwise 1N boron tribromide in dichloromethane (1.5 ml) under ice bath cooling. The mixture was stirred at the same temperature for 2.5 hours. The mixture was poured into 1N hydrochloric acid and extracted with ethyl acetate. The extract was separated, washed with brine, dried over magnesium sulfate and evaporated in vacuo. The residue was purified by silica gel column chromatography (n-hexane: ethyl acetate=1:1) to give 2-[(1,2,3,4-zetrahydro-5-hydroxy-2-naphthyl)methyly] -6-diphenylmethyl-3(2H)-pyridazinone (0.44 g) as a pale yellow oil.

IR (Film): 3000–3500, 1650, 770, 700 cm$^{-1}$; NMR (CDCl$_3$, δ): 1.35–1.66 (1H, m), 1.80–2.00 (1H, m), 2.25–2.90 (5H, m), 4.00–4.30 (2H, m), 5.47 (1H, s), 6.55–6.65 (2H, m), 6.90–7.35 (14H, m); MASS (+APCI): 423 (M$^+$+1)

EXAMPLE 7

A suspension of 2-[(1,2,3,4-tetrahydro-5-hydroxy-2-naphthyl)methyl]-6-diphenylmethyl-3(2H)-pyridazinone (425 mg), ethyl bromoacetate (184 mg) and potassium carbonate (152.9 mg) in acetonitrile (15 ml) was refluxed for 6 hours. After cooling, the precipitated solid was filtered off and the filtrate was evaporated in vacuo. The residue was purified by silica gel column chromatography (n-hexane:ethyl acetate=1:1) to give 2-[(1,2,3,4-tetrahydro-5-ethoxycarbonylmethoxy-2-naphthyi)methyl]-6-diphenylmethyl-3(2H)-pyridazinone (0.43 g) as pale yellow oil.

IR (Film): 1750, 1660, 1580, 760, 720, 700 cm$^{-1}$; NMR (CDCl$_3$, δ): 1.35–1.60 (1H, m), 1.29 (3H, t, J=7.1Hz), 1.80–2.00 (1H, m), 2.20–3.20 (5H, m), 4.15–4.20 (2H, m), 4.25 (2H, q, J=7.1 Hz), 4.61 (2H, s), 5.45 (1H, s), 6.51 (1H, d, J=7.8 Hz), 6.64 (1H, d, J=7.8 Hz), 6.86 (1H, d, J=9.5 Hz), 7.08 (1H, dd, J=7.8 Hz, 7.8 Hz), 7.10–7.35 (11H, m); MASS (+APCI): 509 (M$^+$+1)

EXAMPLE 8

A solution of 2-[(1,2,3,4-tetrahydro-5-ethoxycarbonylmethoxy-2-naphthyl)methyl]-6-diphenylmethyl-3(2H)-pyridazinone (0.43 g) in 1,2-dimethoxyethane (9.0 ml) and 1.0N aqueous solution of sodium hydroxide (0.85 ml) was stirred at room temperature For 5 hours. The solution was evaporated in vacuo and extracted with ethyl acetate and 1N hydrochloric acid. The organic layer was separated and washed with water and brine, dried over magnesium sulfate, and evaporated in vacuo. The residue was crystallized from n-hexane, ethyl acetate and ether to give 2-[(1,2,3,4-tetrahydro-5-carboxymethoxy-2-naphthyl)methyl]-6-diphenylmethyl-3 (2H)-pyridazinone (330 mg) as a white powder.

mp: 176°–178° C.; IR (Nujol): 2600–2200, 1740, 1640, 770, 700 cm$^{-1}$; NMR (DMSO-d$_6$, δ): 1.20–1.45 (1H, m), 1.70–1.90 (1H, m), 2.10–2.90 (5H, m), 3.90–4.10 (2H, m), 4.65 (2H, s), 5.57 (1H, s), 6.55–6.65 (2H, m), 6.90–7.05 (2H, m), 7.20–7.35 (11H, m), 12.96 (1H, br s); MASS (+APCI): 481 (M$^+$+1)

PREPARATION 10

A mixture of (1R,2S)-methyl [1-hydroxy-5-methoxy-1,2,3,4-tetrahydro-2-naphthyl]formate (2.22 g) and 10% palladium on carbon in methanol (50 ml) was stirred under hydrogen (2–3 atm) at room temperature for 22 hours. The catalyst was filtered off and the filtrate was evaporated in vacuo. The residue was purified by silica gel column chromatography (n-hexane:ethyl acetate=4:1) to give (S)-methyl (5-methoxy-1,2,3,4-tetrahydro-2-naphthyl)formate as a colorless oil (1.66 g).

NMR (CDCl$_3$, δ): 1.70–1.90 (1H, m), 2.15–2.30 (1H, m), 2.50–3.00 (5H, m), 3.74 (3H, s), 3.81 (3H, s), 6.60–6.75 (2H, m), 7.05–7.15 (1H, m); MASS (+APCI): 221 (M$^+$+1)

PREPARATION 11

To a mixture of lithium aluminum hydride (0.28 g) in dry tetrahydrofuran (THF) (5 ml) was added dropwise a solution of (S)-methyl [5-methoxy-1,2,3,4-tetrahydro-2-naphthyl] formate (1.65 g) in THF (7 ml) at −60° C. under nitrogen. After 1 hour, a mixture of 1N hydrochloric acid solution (5 ml) and THF (5 ml) was added dropwise to the reaction mixture at −60° C. The reaction mixture was partitioned between ethyl acetate and water. The organic layer was separated, washed with 1N hydrochloric acid solution, sodium hydrogencarbonate solution and brine, dried over magnesium sulfate, and evaporated En vacuo to give (5-methoxy-1,2,3,4-tetrahydro-2-naphthyl)methanol as a white powder (1.23 g).

$[\alpha]_D^{30}$=−71.98° (C=1.26,CH$_2$Cl$_2$) NMR (CDCl$_3$, δ): 1.25–2.20 (4H, m), 2.40–2.65 (2H, m), 2.80–3.00 (2H, m), 3.62 (2H, d, J=6.3 Hz), 3.81 (3H, s), 6.66 (1H, d, J=7.9 Hz), 6.72 (1H, d, J=7.9 Hz), 7.08 (1H, dd, J=7.9 Hz, 7.9 Hz

PREPARATION 12

The following compound was obtained according to a similar manner to that of Preparation 6.

(S)-(5-Methoxy-1,2,3,4-tetrahydro-2-naphthyl)methyl methanesulfonate $[\alpha]_D^{25}$=−45.70° (C=1.00,CH$_2$Cl$_2$); IR (Film): 1580, 340, 1170 cm$^{-1}$; NMR (CDCl$_3$, δ): 1.30–1.60 (1H, m), 1.90–2.30 (2H, m), 2.45–2.70 (2H, m), 2.80–3.00 (2H, m), 3.03 (3H, s), 3.81 (3H, s), 4.20 (2H, d, J=6.5 Hz), 6.60–6.75 (2H, m), 7.00–7.25 (1H, m); MASS (+APCI): 271 (M$^+$+1)

PREPARATION 13

To a solution of methyl (5-methoxy-3,4-dihydro-2-naphthyl)formate (0.75 g) in toluene (10 ml) was added dropwise a solution of diisobutylalminum hydride [1.02N in toluene (6.7 ml)] at 4° C.~6° C. under nitrogen atmosphere. The reaction mixture was stirred under same conditions for 2.5 hours. The mixture was poured into a saturated ammonium chloride solution, and the organic layer was separated, washed with brine, dried over magnesium sulfate, and evaporated in vacuo to give crude (5-methoxy-3,4-dihydro-2-naphthyl)methanol as a colorless oil 40.66 g).

IR (Film): 3700–3100, 1600, 1580 cm$^{-1}$; NMR (CDCl$_3$, δ): 2.28 (2H, t, J=8.5 Hz), 2.85 (2H, t, J=8.5 Hz), 3.83 (3H, s), 4.22 (2H, d, J=4.7 Hz), 6.42 (1H, t, J=1.5 Hz), 6.60–6.80 (2H, m), 7.05–7.15 (1H, m); MASS (+APCI): 173 (M$^+$+1-H$_2$O)

PREPARATION 14

Carbontetrabromide (1.00 g×4) was added portionwise to a solution of 3,4-dihydro-5-methoxy-2-naphthyl)methanol (2.00 g) and triphenyiphosphine (4.14 g) in dichloromethane (40 ml) at room temperature. The reaction mixture was stirred for 2 days and evaporated in vacuo. Hexane and diethyl ether were added to the residue and white powder was filtered off and the filtrate was evaporated in vacuo to give crude 3-bromomethyl-1,2-dihydro-8-methoxynaphthalene as a pale yellow oil.

PREPARATION 15

To a solution of 2-(5-methoxy-1,2,3,4-tetrahydro-1-naphthyl)ethanol (0.20 g) and triphenylphosphine (0.42 g) in dichloromethane (10 ml) was added tetrabromomethane (0.90 g) at 5° C. The solution was stirred at 5° C. for 1.5 hours and evaporated in vacuo. To the residue, ethyl acetate was added and the insoluble material was filtered off. The ethyl acetate solution was evaporated in vacuo. The residue was chromatographed (n-hexane) over silica gel to afford 2-(5-methoxy-1,2,3,4-tetrahydro-1-naphthyl)ethyl bromide (0.18 g) as a colorless oil.

NMR (CDCl$_3$, δ): 1.64–1.85 (4H, m), 2.03–2.29 (2H, m), 2.57–2.76 (2H, m), 2.98–3.02 (1H, m), 3.45–3.60 (2H, m), 3.81 (3H, s), 6.68 (1H, d, J=7.9 Hz), 6.80 (1H, d, J=7.9 Hz), 7.20 (1H, dd, J=7.9, 7.9 Hz); MASS (APCI) m/z: 269, 271 (M$^+$+1)

PREPARATION 16

(S)-2-[(1,2,3,4-Tetrahydro-5-methoxy-2-naphthyl) methyl]-6-diphenylmethyl-3(2H)-pyridazinone was prepared from (S)-(5-methoxy-1,2,3,4-tetrahydro- 2-naphthyl) methyl methanesulfonate in a similar manner to that of Preparation 8.

$[\alpha]_D^{30}$=−29.76° (C=0.86,CH$_2$Cl$_2$); NMR (CDCl$_3$, δ): 1.35–1.55 (1H, m), 1.80–2.00 (1H, m), 2.25–3.00 (5H, m), 3.80 3H, s), 4.05–4.25 (2H, m), 5.45 (1H, s), 6.61 (1H, d, J=6.9 Hz), 6.64 (1H, d, J=6.9 Hz), 6.87 (1H, d, J=9.5 Hz), 7.00–7.35 (12H, m); MASS (+APCI): 437 (M$^+$+1)

PREPARATION 17

To a solution of potassium tert-butoxide (0.39 g) and 18-crown-6 (0.08 g) in dry N,N-dimethylformamide (4 ml) was added 6-diphenylmethyl-3(2H)-pyridazinone (0.83 g) at room temperature. After ten minutes, 3-bromomethyl-1,2-dihydro-8-methoxynaphthalene (0.80 g) was added to the solution and stirred at the same temperature overnight. The reaction mixture was poured into ethyl acetate and 1N hydrochloric acid and the organic layer was separated, washed with water, aqueous sodium hydrogencarbonate solution and brine, dried over magnesium sulfate, and evaporated in vacuo. The residue was purified by silica gel column chromatography (n-hexane:ethyl acetate=1:1) to give 2-[(3,4-dihydro-5-methoxy-2-naphthyl)methyl]-6-diphenylmethyl-3(2H)-pyridazinone (0.55 g).

IR (CH$_2$Cl$_2$): 1670, 1600 cm$^{-1}$; NMR (CDCl$_3$, δ): 2.22 (2H, t, J=8.0 Hz), 2.77 (2H, t, J=8.0 Hz), 3.82 (3H, s), 4.84 (2H, s), 5.44 (1H, s), 6.26 (1H, s), 6.22 (1H, d, J=8.3 Hz), 6.73 (1H, d, J=7.5 Hz), 6.86 (1H, d, J=9.6 Hz), 7.00–7.33 (12H, m); MASS (+APCI): 435 (M$^+$+1)

PREPARATION 18

The following compounds were obtained according to a similar manner to that of Preparation 17.

(1) 1-[(3,4-Dihydro-5-melhoxy-2-naphthyl)methyl]-5-diphenylmethyl-2(1H)-pyridone IR (CH$_2$Cl$_2$): 1670, 1600 cm$^{-1}$; NMR (CDCl$_3$, δ): 2.16 (2H, t, J=8.2 Hz), 2.75 (2H, t, J=8.2 Hz), 3.83 (3H, s), 4.62 (2H, s), 5.23 (1H, s), 6.15 (1H, s), 6.55–6.60 (2H, m), 6.70–6.85 (2H, m), 7.05–7.35 (12H, m); MASS (+APCI): 434 (M$^+$+1)

(2) 1-[(3,4-Dihydro-5-methoxy-2-naphthyl)methyi]-3-diphenylmethyl-2(1H)-pyridone IR (CH$_2$CH$_2$): 1650, 1600 cm$^{-1}$; NMR (CDCl$_3$, δ): 2.18 (2H, t, J=8.2 Hz), 2.79 (2H, t, J=8.2 Hz), 3.81 (3H, s), 4.71 (2H, s), 5.82 (1H, s), 6.11 (1H, t, J=6.8 Hz), 6.24 (1H, s), 6.60–6.90 (3H, m), 7.05–7.35 (12H, m); MASS (+APCI): 434 (M$^+$+1)

PREPARATION 19

To a solution of 6-diphenylmethyl-3(2H)-pyridazinone (0.22 g) and potassium tert-butoxide (0.10 g) in N,N-dimethylformamide (2 ml) was added a solution of 2-(5-methoxy-1,2,3,4-tetrahydro-1-naphthyl)ethyl bromide (0.18 g) in N,N-dimethylformamide (3 ml) at room temperature. The reactIon mixture was stirred for 2 hours at the same temperature and partitioned between water and ethyl acetate. The organic layer was washed with water (3 times) and brine, dried over sodium sulfate, and evaporated in vacuo. The residue was chromatographed (n-hexane - ethyl acetate) over silica gel to afford 2-[2-(5-methoxy-1,2,3,4-tetrahydro-1-naphthyl)ethyl]-6-diphenylmethyl-3(2H)-pyridazinone (0.25 g) as an oil.

NMR (CDCl$_3$, δ): 1.65–2.05 (4H, m), 2.10–2.28 (1H, m), 2.50–2.85 (3H, m), 3.80 (3H, s), 4.07–4.33 (3H, m), 5.46 (1H, s), 6.64 (1H, d, J=8.5 Hz), 6.69 (1H, d, J=9.4 Hz), 6.84 (1H, d, J=9.4 Hz), 7.02–7.36 (12H, m); MASS (APCI) (m/z): 451 (M$^+$−1)

PREPARATION 20

The following compounds were obtained according to a similar manner to that of Preparation 9.

(1) (S)-2-[(1,2,3,4-Tetrahydro-5-hydroxy-2-naphthyl)methyl]-6-diphenylmethyl-3(2H)-pyridazinone

[α]$_D^{25}$=−30.280 (C=1.04, CH$_2$Cl$_2$); IR (Film): 3500–3000, 1650, 770, 700 cm$^{-1}$; NMR (CDCl$_3$, δ): 1.35–1.60 (1H, m), 1.80–2.00 (1H, m), 2.25–2.90 (5H, m), 4.00–4.30 (2H, m), 5.47 (1H, s), 6.55–6.65 (2H, m), 6.90–7.35 (14H, m); MASS (+APCI): 423 (M$^+$+1)

(2) 2-[(3,4-Dihydro-5-hydroxy-2-naphthyl)methyl]-6-diphenylmethyl-3(2H)-pyridazinone mp: 174°–176° C.; IR (Nujol): 3200, 1650 cm$^{-1}$; NMR (DMSO-d$_6$, δ): 2.09 (2H, t, J=8.2 Hz), 2.62 (2H, t, J=8.2 Hz), 4.72 (2H, s), 5.56 (1H, s), 6.09 (1H, s), 6.45 (1H, d, J=7.2 Hz), 6.65 (1H, d, J=7.2 Hz), 6.85–6.95 (2H, m), 7.15–7.40 (11H, m), 9.23 (1H, s); MASS (+APCI): 421 (M$^+$+1)

(3) 1-[(3,4-Dihydro-5-hydroxy-2-naphthyl)methyl]-5-diphenylmethyl-2(1H)-pyridone mp: 178°–180° C.; IR (Nujol): 3150, 1650 cm$^{-1}$; NMR (CDCl$_3$, δ): 2.15 (2H, t, J=8.2 Hz), 2.70 (2H, t, J=8.2 Hz), 4.62 (2H, s), 5.26 (1H, s), 6.11 (1H, s), 6.54 (1H, d, J=7.3 Hz), 6.65–6.75 (2H, m) 6.85 (1H, d, J=2.5 Hz), 6.95–7.33 (13H, m); MASS (+APCI) 420 (M$^+$+1)

(4) [(3,4-Dihydro-5-hydroxy-2-naphthyl)methyl]-3-diphenylmethyl-2(1H)-pyridone mp: 196°–197° C.; IR (Nujol): 3250, 1640 cm$^{-1}$; NMR (DMSO-d$_6$, δ): 2.10 (2H, t, J=8.3 Hz), 2.64 (2H, t, J=8.3 Hz), 4.63 (2H, s), 5.65 (1H, s), 5.96 (1H, s), 6.24 (1H, t, J=6.8 Hz), 6.42 (1H, d, J=7.2 Hz), 6.64 (1H, d, J=7.5 Hz), 6.85–7.35 (12H, m), 7.55–7.60 (1H, m), 9.24 (1H, s); MASS (+APCI): 420 (M$^+$+1)

PREPARATION 21

A mixture of (1,2,3,4-tetrahydro-5-hydroxy-2- naphthyl) methyl N,N-diphenylcarbamate (100 mg) and N-chlorosuccinimide (35.8 mg) in 1,4-dioxane (1.5 ml) was stirred at 100° C. for 5 hours, cooled to room temperature, and partitioned between ethyl acetate and brine. The organic layer was washed with brine, dried over magnesium sulfate, and evaporated in vacuo. The residue was chromatographed (toluene-ethyl acetate) over silica gel to afford (6- or 8-chloro-1,2,3,4-tetrahydro-5-hydroxy-2-naphthyl)methyl N,N-diphenylcarbamate (62 mg) as colorless solids.

mp: 138°–144° C.; IR (Nujol): 3320, 1675, 1575, 1220 cm$^{-1}$; NMR (CDCl$_3$, δ): 1.20–1.41 (1H, m), 1.85–2.1 (2H, m), 2.18–2.32 (1H, m), 2.42–2.56 (1H, mn), 2.74–2.94 (2H, m), 4.07–4.28 (2H, m), 4.91 (1H, s), 6.54 (1H, d, J=8.5 Hz), 7.05 (1H, d, J=8.5 Hz), 7.16–7.39 (10H, m); (+) APCI MS m/z: 408 (M$^+$+1)

PREPARATION 22

A solution of diethyl azodicarboxylate (871 mg) in tetrahydrofuran (4 ml) was added slowly to a stirred solution of (1,2,3,4-tetrahydro-5-methoxy-2-naphthyl)methanol (961 mg), phthalimide (736 mg), and triphenylphosphine (1.31 g) in tetrahydrofuran (10 ml) at room temperature and the resulting mixture was stirred at the same temperature for 24 hours. The reactIon mixture was evaporated in vacuo and the residue was chromatographed (toluene) over silica gel. The eluate was evaporated in vacuo and the residue was triturated with n-hexane to afford N-[(1,2,3,4-tetrahydro-5-methoxy-2-naphthyl)methyl]phthalimide (888 mg) as a colorless powder.

mp: 143°–144° C.; IR (Nujol): 1770, 1705, 1580, 1260 cm$^{-1}$; NMR (CDCl$_3$, δ): 1.33–1.55 (1H, m), 1.93–2.03 (1H, m), 2.15–2.25 (1H, m), 2.35–2.63 (2H, m), 2.75–2.97 (2H, m), 3.71 (2H, d, J=7.1 Hz), 3.79 (3H, s), 6.62–6.69 (2H, m), 7.06 (1H, t, J=7.9 Hz), 7.68–7.77 (2H, m), 7.82–7.90 (2H, m); (+) APCI MS m/z: 322 (M$^+$+1)

PREPARATION 23

The following compound was obtained according to a similar manner to that of Preparation 4.

N-[(1,2,3,4-Tetrahydro-5-hydroxy-2-naphthyl)methyl]-phthalimide

IR (Nujol): 3310, 1765, 1690, 1585 cm$^{-1}$; NMR (DMSO-d$_6$, δ): 1.38 (1H, m), 1.91 (1H, m), 2.05 (1H, m), 2.34–2.5 (2H, m), 2.69–2.77 (2H, m), 3.58 (2H, d, J=7.0 Hz), 6.47 (1H, d, J=7.4 Hz), 6.56 (1H, d, J=7.4 Hz), 6.86 (1H, t, J=7.4 Hz) 7.81–7.93 (4H, m), 9.15 (1H, s); (+) APCI MS m/z: 308 (M$^+$+1)

PREPARATION 24

A solution of N-[(1,2,3,4-tetrahydro-5-hydroxy-2-naphthyl)methyl]phthalimide (634 mg) and hydrazine monohydrate (309 mg) in ethanol (14 ml) was refluxed for 3 hours, cooled to room temperature, and evaporated in vacuo. The residue was chromatographed (methylene chloride-methanol) over basic alumina to afford 6-(aminomethyl)-5,6,7,8-tetrahydro-1-naphthol (281 mg) as a colorless powder.

mp: 183°–192° C.; IR (Nujol): 3350–3100, 2750–2300, 1580 cm$^{-1}$; NMR (DMSO-d$_6$, δ): 1.11–1.32 (1H, m), 1.58

(1H, m), 1.91–1.97 (1H, m), 2.23–2.45 (2H, m), 2.68–2.80 (2H, m), 3.1 (3H, br), 6.49 (1H, d, J=7.6 Hz), 6.55 (1H, d, J=7.8 Hz), 6.85 (1H, t, J=7.7 Hz); (+) APCI MS m/z: 178 ($M^+$+1)

PREPARATION 25

A solution of 4-nitrophenyl chloroformate (2.02 g) in dichloromethane (15 ml) was added dropwise to a stirred solution of benzhydrol (1.84 g) and pyridine (1.19 g) in dichioromethane (18 ml) under ice cooling. The resulting mixture was stirred at the same temperature for a while and allowed to stand at room temperature for 3 days. The reaction mixture was washed successively with ice-water, ice-1N hydrochloric acid, and ice-brine, dried over magnesium sulfate, and evaporated in vacuo. The residue was chromatographed (toluene-ethyl acetate) over silica gel to afford benzhydryl (4-nitrophenyl)carbonate (3.32 g) as colorless crystals.

mp: 53°–59° C.; IR (Film): 1770, 1520, 1345, 1260–1180 $cm^{-1}$; NMR ($CDCl_3$, δ): 6.81 (1H, s), 7.30–7.47 (12H, m), 8.25 (2H, d, J=9.2 Hz); (+) APC-MS m/z: 167

PREPARATION 26

A solution of 6-aminomethyl)-5,6,7,8-tetrahydro-1-naphthol (23 mg) and 4-nitrophenyl(benzhydryl)carbonate (45 mg) in N,N-dimethylformamide (0.5 ml) was stirred at 50° C. for 2 hours, cooled to room temperature, and extracted with ethyl acetate. The extract was washed successively with water, sodium bicarbonate aqueous solution (three times) and brine, dried over magnesium sulfate, and evaporated in vacuo. The residue was chromatographed (toluene-ethyl acetate) over silica gel to afford benzhydryl N-[(1,2,3,4-tetrahydro-5-hydroxy-2-naphthyl)methyl] carbamate (40 mg) as an oil.

IR (Film): 3350, 1695 $cm^{-1}$; NMR ($CDCl_3$, δ): 1.35–1.45 (1H, m), 1.94 (2H, m), 2.45–2.6 (2H, m), 2.76–2.86 (2H, m), 3.22 (2H, t, J=6.3 Hz), 5.04 (1H, m), 6.58 (1H, d, J=7.9 Hz), 6.64 (1H, d, J=7.6 Hz), 6.31 (1H, s), 6.97 (1H, t, J=7.8 Hz), 7.15–7.35 (11H, m); (+) APCI MS m/z: 167

PREPARATION 27

(6RS)-5,6,7,8-Tetrahydro-6-[((1S)-1-phenylethyl)-amino]-1-naphthol was prepared from (2RS)-1,2,3,4-tetrahydro-5-methoxy-N-((1S)-1-phenylethyl)-2-naphthylamine hydrochloride in a similar manner to that of Preparation 9.

IR (Film): 3500–3350, 1585 $cm^{-1}$; NMR ($CDCl_3$, δ): 1.38 (3H, d, J=6.6 Hz), 1.5–2.2 (3H, m), 2.45–2.65 (2H, m), 2.75–2.85 (2H, m), 4.05 (1H, q, J=6.6 Hz), 6.4–7.35 (9H, m); (+) APCI MS m/z: 268 ($M^+$+1)

PREPARATION 28

A solution of (6RS)-5,6,7,8-tetrahydro-6-[((1S)-1-phenylethyl)amino]-1-naphthol (267 mg) in dimethylsulfoxide (3 ml) was added dropwise to a stirred suspension of 60% sodium hydride (44 mg, washed with n-hexane) in dimethylsulfoxide (0.5 ml) at room temperature in a nitrogen atmosphere over 15 minutes, and the mixture was stirred at 50° C. for 10 minutes and cooled to room temperature. Ethyl bromoacetate (167 mg) in dimethylsulfoxide (1 ml) was added thereto and the resulting mixture was stirred at the same temperature for 2 hours. The reaction mixture was poured into ice-water and extracted with ethyl acetate. The extract was washed twice with brine, dried over sodium sulfate, and evaporated in vacuo. The residue was chromatographed (dichloromethane-ethanol) over silica gel to afford ethyl [(6RS)-5,6,7,8-tetrahydro-6-[((1S)-1-phenylethyl) amino]-1-naphthyloxy]acetate (243 mg) as a brown oil.

IR (Film): 3320, 1755, 1730 (shoulder), 1585, 1195 $cm^{-1}$; NMR ($CDCl_3$, δ): 1.25 (3H, t, J=7.1 Hz), 1.37 (3H, d, J=6.6 Hz), 1.48 (3H, br m), 2.09 (1H, br m), 2.48–3.02 (4H, m), 4.04 (1H, q, J=6.6 Hz), 4.25 (2H, q, J=7.1 Hz), 4.58 (2H, s), 6.49 (1H, d, J=8.0 Hz), 6.67 (1H, d, J=8.0 Hz), 7.01 (1H, t, J=8.0 Hz), 7.20–7.33 (5H, m); (+) APCI MS: 354 ($M^+$+1)

PREPARATION 29

Ethyl [(6RS)-5,6,7,8-tetrahydro-6-[((1S)-1-phenylethyl) amino]-1-naphthyloxy]acetate (185 mg) was converted to the hydrochloride using 4N hydrogen chloride in ethyl acetate in a usual manner. A mixture of the hydrochloride, 10% palladium on carbon (50% wet, 100 mg), and ammonium formate (330 mg) in ethanol (40 ml) was stirred under reflux for 30 minutes and the hot reaction mixture was filtered. The filtrate was evaporated in vacuo and the residue was partitioned between ethyl acetate and sodium bicarbonate aqueous solution. The ethyl acetate layer was dried over sodium sulfate and evaporated in vacuo to ethyl [(6RS)-6-amino-5,6,7,8-tetrahydro-1-naphthyloxy)acetate (95 mg) as an oil.

IR (Film): 3600–3150, 1750, 1730 (shoulder), 1580, 1195 $cm^{-1}$; NMR ($CDCl_3$, δ): 1.30 (3H, t, J=7.1 Hz), 1.46–1.66 (3H, m), 2.01 (1H, m), 2.48–2.78 (2H, m), 2.92–3.16 (3H, m), 4.26 (2H, q, J=7.1 Hz), 4.62 (2H, s), 6.53 (1H, d, J=8.0 Hz), 6.74 (1H, d, J=7.6 Hz), 7.05 (1H, t, J=7.8 Hz)

PREPARATION 30

A suspension of (5-hydroxy-1,2,3,4-tetrahydro-1-naphthyl)methanol (0.20 g), ethyl bromoacetate (0.15 ml), potassium iodide (catalytic amount) and potassium carbonate (0.20 g) in acetonitrile (10 ml) was stirred under reflux for 2.5 hours. The solvent was removed and the residue was partitioned between ether and 1N hydrochloric acid. The organic layer was washed with water and brine, dried over sodium sulfate, and evaporated in vacuo. The residue was chromatographed (n-hexane-ethyl acetate) over silica gel to afford (5-ethoxycarbonylmethoxy-1,2,3,4-tetrahydro-1-naphthyl)methanol (0.29 g) as an oil.

IR (Film): 3400, 1730 $cm^{-1}$; NMR ($CDCl_3$, δ): 1.44 (1H, t, J=5.4 Hz), 1.80–1.95 (4H, m), 2.63–2.98 (3H, m), 3.80 (2H, dd, J=5.4, 5.4 Hz), 4.26 (2H, q, J=7.1 Hz), 4.62 (2H, s), 6.56 (1H, d, J=7.9 Hz), 6.89 (1H, d, J=7.9 Hz), 7.09 (1H, dd, J=7.9, 7.9 Hz) MASS (APCI) m/z: 265 ($M^+$+1), 247 ($M^+$+1 -$H_2O$)

PREPARATION 31

To a solution of diethylcarbonate (10.3 ml) and sodium hydride (4.2 g, 60%, in oil) in toluene (300 ml) was added 5-t-butyldiphenylsilyloxy-1-oxo-1,2,3,4-tetrahydronaphthalene (17 g) at 100° C. The mixture was stirred for 4 hours at the same temperature and then the cooled solution was washed with sat. $NaHCO_3$ and brine. The dried solvent was evaporated in vacuo and the residue was purified by chromatography on silica gel to give 5-t-butyldiphenylsilyloxy-2-ethoxycarbonyl-1-oxo-1,2,3,4-tetrahydronaphthalene (20 g).

IR (neat): 1730, 1680 $cm^{-1}$; NMR ($CDCl_3$, δ): 1.11 (9H, s), 1.25 (3H, t, J=7 Hz), 2.3–2.7 (2H, m), 2.8–3.4 (2H, m), 3.60 (1H, dd, J=5.2, 10.4 Hz), 4.28 (2H, q, J=7 Hz), 6.4–6.8 (2H, m), 7.2–7.8 (11H, m); MS m/z: 473 ($M^+$+1)

PREPARATION 32

To a solution of 5-t-butyldiphenylsilyloxy-2-ethoxycarbonyl-1-oxo-1,2,3,4-tetrahydronaphthalene (17 g)

in a mixture of ethanol (100 ml) and tetrahydrofuran (100 ml) was added NaBH$_4$ (1.4 g) at 0° C. After the mixture was stirred for 6 hours at room temperature, the solvent was removed in vacuo. The residue was dissolved in a mixture of ethyl acetate and water and the organic solution was washed with 1N-HCl solution, sat. NaHCO$_3$, and brine. The dried solvent was evaporated in vacuo and the residue was purified by chromatography on silica gel to give 1-hydroxy-2-ethoxycarbonyl-5-t-butyldiphenylsilyloxy-1,2,3,4-tetrahydronaphthalene (7.9 g).

IR (neat): 3450, 1730 cm$^{-1}$; NMR (CDCl$_3$, δ): 1.10 (9H, s), 1.26 (3H, t, J=7 Hz), 2.2–2.5 (2H, m), 2.5–3.4 (4H, m), 4.16 (2H, q, J=7 Hz), 5.02 (1H, m), 6.2–6.4 (1H, m), 6.7–7.0 (2H, m), 7.2–7.8 (10H, m)

PREPARATION 33

To a solution of 1-hydroxy-2-ethoxycarbonyl-5-t-butyldiphenylsilyloxy-1,2,3,4-tetrahydronaphthalene (5.9 g) in toluene (100 ml) was added KHSO$_4$ (2.0 g). The mixture was stirred for 1 hour under reflux, and then the cooled solution was washed with sat. NaHCO$_3$ and brine. The dried solvent was evaporated in vacuo and the residue was purified by chromatography on silica gel to give 2-ethoxycarbonyl-5-t-butyldiphenylsilyloxy-3,4-dihydronaphthalene (7.4 g).

IR (neat): 1700 cm$^{-1}$; NMR (CDCl$_3$, δ): 1.11 (9H, s), 1.35 (3H, t, J=7 Hz), 2.5–2.7 (2H, m), 3.03 (2H, t, J=8.8 Hz), 4.27 (2H, q, J=7 Hz), 6.3–6.5 (1H, m), 6.7–6.8 (2H, m), 7.1–7.8 (11H, m); MS m/z: 457 (M$^+$+1)

PREPARATION 34

A solution of AD-mix-α (trade name, Aldrich) (9.2 g) in a mixture of t-butyl alcohol (30 ml) and water (30 ml) was stirred for 1 hour and then methanesulfonamide (0.62 g) and 2-ethoxycarbonyl-5-t-butyldiphenylsilyloxy-3,4-dihydronaphthalene (3.0 g) were added to the solution at room temperature. After being stirred for 20 hours at the same temperature, sodium sulfite (9.0 g) was added, and the mixture was stirred for 30 minutes. The mixture was partitioned between ethyl acetate and water. The organic layer was washed with 1N-HCl solution, sat. NaHCO$_3$, and brine, dried over MgSO$_4$, and evaporated in vacuo. The residue was purified by chromatography on silica gel to afford (1S,2R)-1,2-dihydroxy-2-ethoxycarbonyl-5-t-butyldiphenylsilyloxy-1,2,3,4-tetrahydronaphthalene (3.1 g).

IR neat): 3450, 1705 cm$^{-1}$; NMR (CDCl$_3$, δ): 1.09 (9H, s), 1.25 (3H, t, J=7.0 Hz), 2.1–2.3 (2H, m), 2.50 (1H, d, J=10.8 Hz), 2.9–3.2 (2H, m), 3.58 (1H, s), 4.35 (2H, q, J=7.0 Hz), 5.03 (1H, d, J=10.8 Hz), 6.32 (1H, d, J=8.0 Hz), 6.80 (1H, t, J=8.0 Hz), 7.14 (1H, d, J=8.0 Hz), 7.3–7.8 (10H, m); MS m/z: 470 (M$^+$–17); HPLC : chiralcel AD, 5% isopropanol/hexane, 12.9 ml/min

PREPARATION 35

The following compound was obtained by using AD-mix-β (trade name, Aldrich) instead of AD-mix-α in a similar manner to that of Preparation 34.

(1R,2S)-1,2-Dihydroxy-2-ethoxycarbonyl-5-t-butyldiphenylsilyloxy-1,2,3,4-tetrahydronaphthalene HPLC chiralcel AD, 5% isopropanol/hexane, 11.0 ml/min

PREPARATION 36

To a solution of 2-methoxycarbonyl-5-methoxy-1-oxo-1,2,3,4-tetrahydroraphthalene (3.9 g) in tetrahydrofuran (50 ml) were added NaH (0.73 g, 60% in oil) and then methyl iodide (3 ml) at 0° C. under N$_2$. After being stirred for 1 hour at room temperature, The solution was poured into a mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 2-methyl-2-methoxycarbonyl-5-methoxy-1-cxo-1,2,3,4-tetrahydronaphthalene (4.0 g).

IR (Neat): 1720, 1680 cm$^{-1}$; NMR (CDCl$_3$, δ): 1.49 (3H, s), 1.9–2.1 (1H, m), 2.4–3.0 (3H, m), 3.66 (3H, m), 3.88 (3H, m), 7.01 (1H, d, J=8 Hz), 7.26 (1H, t, J=8 Hz), 7.68 (1H, d, J=8 Hz); MS m/z: 249 (M$^+$+1)

PREPARATION 37

To a solution of 2-methyl-2-methoxycarbonyl-5-methoxy-1-oxo-1,2,3,4-tetrahydronaphthalene (2.0 g) in trifluoroacetic acid (20 ml) was added triethyls4lane (2.0 ml) at room temperature. After being stirred for 6 hours at room temperature, the solution was poured into a mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 2-methyl-2-methoxycarbonyl-5-methoxy-1,2,3,4-tetrahydronaphthalene (4.0 g).

IR (neat): 1720 cm$^{-1}$; NMR (CDCl$_3$, δ): 1.25 (3H, s), 1.6–2.3 (2H, m), 2.5–2.8 (3H, m), 3.20 (1H, d, J=16 Hz), 3.66 (3H, m), 3.80 (3H, m), 6.64 (1H, d, J=8 Hz), 6.70 (1H, d, J=8 Hz), 7.08 (7H, t, J=8 Hz); MS m/z: 235 (M$^+$+1)

PREPARATION 38

To a solution of diethyiphosphoric acid ethyl ester (19 g) in dimethoxyethane (200 ml) was added NaH (3.4 g, 60%) in oil) at 0° C. under N$_2$. After being stirred for 30 minutes, 5-t-butyidiphenylsilyloxy-1-oxo-1,2,3,4-tetrahydronaphthalene (20 g) was added to the mixture. After being stirred for 12 hours at 80° C., the solution was poured hnto a mixture of ethyl acetate and water. The organic layer was washed with 1N-HCl solution, sat. NaHCO$_3$, and brine, dried over MgSO$_4$, and evaporated in vacuo. The residue was dissolved into a mixture of toluene (100 ml and 1,8-diazabicyclo[5.4.0]-7-undecene (17 ml) and the mixture was stirred for 3 days at 100° C. The solution was washed with 1N-HCl solution, sat. NaHCO$_3$, and brine, dried over MgSO$_4$, and evaporated in vacuo. The residue was purified by chromatography on silica gel to afford 5-t-butyldiphenylsilyloxy-1-ethoxycarbonylmethyl-3,4-dihydronaphthalene (20.3 g).

IR (neat): 1740 cm$^{-1}$; NMR (CDCl$_3$, δ): 1.10 (9H, m), 1.25 (3H, t, J=7 Hz), 2.2–2.4 (2H, m), 2.99 (2H, t, J=8.2 Hz), 3.40 (2H, s), 4.17 (2H, q, J=7 Hz), 6.00 (1H, m), 6.3–6.5 (1H, m), 6.6–6.8 (2H, m), 7.3–7.8 (10H, m); MS m/z: 471 (M$^+$+1)

PREPARATION 39

To a solution of diisopropylamine (17 ml) in THF (tetrahydrofuran) (210 ml) was added n-butyllithium (67 ml, 1.6N in hexane) at –78° C. under N$_2$. The solution was stirred for 30 minutes at 0° C. and then cooled to –78° C. To the solution was added ethyl acetate (12 g) and the mixture was stirred for 30 minutes at the same temperature to give Li-enolate solution. A solution of 5-t-butyldiphenylsilyloxy-1-oxo-1,2,3,4-tetrahydronaphthalene (10 g) in THF (50 ml) was cooled to –78° C., the above Li-enolate solution (35 ml)

was added, and stirred for 1 hour at the same temperature. The mixture was poured into a mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 1-hydroxy-1-ethoxycarbonylmethyl-5-t-butyldiphenylsilyloxy-2,3,4-tetrahydronaphtalene (8.0 g).

IR (neat): 3400, 1705 cm$^{-1}$; NMR (CDCl$_3$, δ): 1.10 (9H, s), 1.27 (3H, t, J=7 Hz), 1.6–2.2 (4H, m), 2.7–3.0 (4H, m), 4.20 (2H, q, J=7 Hz), 6.30 (1H, d, J=8 Hz), 6.77 (1H, t, J=8 Hz), 7.10 (1H, d, J=8 Hz), 7.2–7.8 (10 H, m); MS m/z: 471 (M$^+$–17)

PREPARATION 40

(1) To a solution of (1S,2R)-1,2-dihydroxy-2-ethoxycarbonyl-5-t-butyldiphenylsilyloxy-1,2,3,4-tetrahydronaphthalene (1.8 g) in CH$_2$Cl$_2$ (20 ml) were added triphenylphosphine (2.9 g) and CBr$_4$ (4.9 g) at the room temperature. After being stirred for 1 hour, ethyl acetate (200 ml) was added to the solution. After filtration, mother liquid was washed with water, sat. NaHCO$_3$, and brine. The dried solvent was evaporated in vacuo to give a residue.

(2) The residue obtained above was purified by chromatography on silica gel. The obtained oil was dissolved into tetrahydrofuran (30 ml) and LiAlH$_4$ (420 mg) was added at 0° C. The mixture was stirred for 2 hours at the same temperature, quenched with 1N-HCl, and partitioned between ethyl acetate and water. The organic layer was washed with water, sat. NaHCO$_3$, and brine. The dried solvent was evaporated in vacuo and the residue was purified by chromatography on silica gel to give (2R)-2-hydroxy-2-hydroxymethyl-5-t-butyldiphenylsilyloxy-1,2,3,4-tetrahydronaphthalene (1.8 g).

IR (neat): 3500, 1600 cm$^{-1}$; NMR (CDCl$_3$, δ): 1.10 (9H, s), 1.8–2.0 (4H, m), 2.85 (2H, s), 3.00 (2H, t, J=7.0 Hz), 3.59 (2H, m), 6.29 (1H, d, J=8.0 Hz), 6.6–6.8 (2H, m), 7.3–7.8 (10H, m); MS m/z: 397 (M$^+$–35)

PREPARATION 41

The following compound was obtained according go a similar manner to that of Preparation 40.

(2S)-2-Hydroxy-2-hydroxymethyl-5-t-butyldiphenylsilyloxy-1,2,3,4-tetrahydronaphthalene

PREPARATION 42

The following compound was obtained according to a similar manner to that of Preparation 1.

5-t-Butyldiphenylsilyloxy-1-(2-hydroxyethyl)-3,4-dihydronaphthalene

IR (neat): 3400–3300 cm$^{-1}$; NMR (CDCl$_3$, δ): 1.06 (9H, s), 2.2–2.4 (2H, m), 2.6–3.0 (4H, m), 3.76 (2H, t, J=6.4 Hz), 5.96 (1H, m), 6.36 (1H, d, J=8 Hz), 6.7–6.9 (2H, m), 7.2–7.8 (10H, m); MS m/z: 429 (M$^+$+1)

PREPARATION 43

To a solution of 5-t-butyldiphenylsilyloxy-2-hydroxymethyl-3,4-dihydronaphthalene (1.0 g) in benzene (10 ml) were added diethylzinc (7.2 ml, 1M solution in hexane) and diiodomethane (1.2 ml) at 0° C. under N$_2$. After being stirred for 4 hours at room temperature, the solution was poured into a mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 5-t-butyldiphenylsilyloxy-1,2-methylene-2-hydroxymethyl-1,2,3,4-tetrahydronaphthalene.

PREPARATION 44

The following compound was obtained according to a similar manner to that of Preparation 43.

1,2-Methylene-1-(2-hydroxyethyl)-5-t-butyldiphenyisilyloxy-1,2,3,4-tetrahydronaphthalene IR (neat): 3400–3300, 1700 cm$^{-1}$; NMR (CDCl$_3$, δ): 0.7–0.9 (2H, m), 1.08 (9H, s), 1.2–1.5 (2H, m), 1.7–2.5 (3H, m), 2.6–2.9 (1H, m), 3.1–3.3 (1H, m), 3.7–3.9 (2H, m), 6.27 (1H, d, J=8 Hz), 6.72 (1H, t, J=8 Hz), 6.99 (1H, d, J=8 Hz), 7.2–7.8 (10H, m); MS m/z: 443 (M$^+$+1)

PREPARATION 45

To a solution of 5-t-butyldiphenylsilyloxy-1-(2-hydroxyethyl)-3,4-dihydronaphthalene (1.0 g) in CH$_2$Cl$_2$ (30 ml) were added Na$_2$CO$_3$ (290 mg) and m-chloroperbenzoic acid (750 mg) at 0° C. After being stirred for 2 hours, the solvent was removed in vacuo. The residue was extracted with ethyl acetate. The mixture was washed with 1N-HCl solution, sat. NaHCO$_3$, and brine, dried over MgSO$_4$, and evaporated in vacuo. The residue was dissolved into tetrahydrofuran (20 ml) and LiAlH$_4$ (200 mg) was added at 0° C. After being stirred for 2 hours, the reaction was quenched by saturated potassium sodium tartrate solution. After filtration, the solvent was removed, and the residue was purified by chromatography on silica gel to afford (cis)-5-t-butyldiphenylsilyloxy-1-(2-hydroxyethyl)-2-hydroxy-1,2,3,4-tetrahydronaphthalene (1.1 g).

IR (neat): 3300 cm$^{-1}$; NMR (CDCl$_3$, δ): 1.10 (9H, s), 1.8–2.3 (4H, m), 2.8–3.2 (3H, m), 3.6–4.2 (3H, m), 6.2–6.4 (1H, m), 6.6–6.8 (2H, m), 7.0–7.8 (10H, m); MS m/z: 429 (M$^+$–17)

PREPARATION 46

A mixture of (2R)-2-hydroxy-2-hydroxymethyl-5-t-butyldiphenylsilyloxy-1,2,3,4-tetrahydronaphthalene (1.4 g) and N,N-diphenylcarbamoyl chloride (3 g) in pyridine (15 ml) was stirred at 100° C. for 12 hours, cooled to room temperature, and partitioned between ethyl acetate and 1N-HCl. The organic layer was washed with water, sat. NaHO$_3$, and brine. The dried solvent was evaporated in vacuo and the residue was purified by chromatography on silica gel to give (2R)-2-hydroxy-2-(N,N-diphenylcarbamoyloxymethyl)-5-t-butyldiphenylsilyloxy-1,2,3,4-tetrahydronaphthalene (1.3 g).

IR (neat): 3400, 1700 cm$^{-1}$; NMR (CDCl$_3$, δ): 1.10 (9H, s), 1.8–2.0 (3H, m), 2.6–3.1 (4H, m), 4.16 (2H, s), 6.25 (1H, d, J=8.0 Hz), 6.53 (1H, d, J=8 Hz), 6.68 (1H, t, J=8 Hz), 7.2–7.8 (20H, m); MS m/z: 628 (M$^+$+1)

HPLC chiralcel OD, 10% isopropanol/hexane, 12.0 mil/min

PREPARATION 47

The following compounds were obtained according to a similar manner to that of Preparation 46.

(1) (2S)-2-Hydroxy-2-(N,N-diphenylcarbamoyloxymethyl)-5-t-butyldiphenylsilyloxy-1,2,3,4-tetrahydronaphthalene HPLC chiralcel OD, 10% isopropanol/hexane, 10.1 ml/min (2) (cis)-1-Hydroxy-2-(N,N-diphenylcarbamoyloxymethyl)-5-t-butyldiphenylsilyloxy-1,2,3,4-tetrahydronaphthalene NMR (CDCl$_3$, δ): 1.08 (9H, s), 1.6–2.1 (3H, m), 2.5–3.2 (2H, m), 4.0–4.2 (1H, m), 4.4–4.8 (2H, m,), 6.32 (1H, d, J=8 Hz), 6.6–6.9 (2H, m), 7.1–7.8 (20H, m); MS m/z: 610 (M$^+$−1);

(3) (trans)-1-Hydroxy-2-(N,N-diphenylcarbamoyloxymelhyl)-5-t-butyldiphenylsilyloxy-1,2,3,4-tetrahydronaphthalene NMR (CDCl$_3$, δ): 1.08 (9H, s), 1.4–2.1 (3H, m), 2.6–3.1 (2H, m), 4.13 (1H, dd, J=11.2, 5.2 Hz), 4.48 (1H, d, J=8 Hz), 4.62 (1H, dd, J=11.2, 4.4 Hz), 6.30 (1H, d, J=8 Hz), 6.77 (1H, t, J=8 Hz), 7.08 (1H, d, J=8 Hz), 7.1–7.8 (20H, m); MS m/z: 610 (M$^+$−1)

(4) 5-t-Butyldiphenylsilyloxy-1,2-methylene-2-(N,N-diphenylcarbamoyloxymethyl)-1,2,3,4-tetrahydronaphthalene IR (neat): 1700 cm$^{-1}$; NMR (CDCl$_3$, δ): 0.8–1.2 (2H, m), 1.6–1.9 (2H, m), 2.0–2.3 (1H, m), 3.1–3.4 (1H, m), 4.20 (1H, d, J=11.2 Hz), 4.30 (1H, d, J=11.2 Hz), 6.25 (1H, d, J=8 Hz), 6.6–7.0 (2H, m), 7.1–7.8 (20H, m)

(5) 5-t-Butyldiphenylsilyloxy-1,2-methylene-1-[2-(N,N-diphenylcarbamoyloxy)ethyl]-1,2,3,4-tetrahydronaphthalene IR (neat): 1700 cm$^{-1}$; NMR (CDCl$_3$, δ): 0.6–0.9 (2H, m), 1.08 (9H, s), 1.2–2.5 (5H, m), 2.6–3.1 (2H, m), 4.0–4.4 (2H, m), 6.24 (1H, d, J=8 Hz), 6.65 (1H, t, J=8 Hz), 6.96 (1H, d, J=8 Hz), 7.1–7.8 (20H, m)

(6) 1-;2-(N,N-Diohenyicarbamnoyloxy)vethy-]-5-t-butyldiphenylsilyloxy-3,4-dihydronaphthalene IR (neat): 1705 cm$^{-1}$; NMR (CDCl$_3$, δ): 1.10 (9H, s), 2.1–2.3 (2H, m), 2.72 (2H, t, J=6.6 Hz), 2.90 (2H, t, J=8.0 Hz), 4.30 (2H, t, J=7.0 Hz), 5.78 (1H, t, J=4.4 Hz), 6.33 (1H d, J=8 Hz), 6.6–6.9 (2H, m), 7.1–7.8 (20H, m); MS m/z: 624 (M$^+$+1)

(7) (cis)-5-t-Buityidiphenyisilyloxy-1-[2-(N,N-diphenylcarbamoyloxy)ethyl]-2-hydroxy-1,2,3,4-tetrahydronaphthaiene IR (neat): 1700 cm$^{-1}$; NMR (CDCl$_3$, δ): 1.10 (9H, s), 1.6–2.3 (4H, m), 2.7–3.2 (3H, m), 4.0–4.4 (3H, m), 6.25 (1H, d, J=8 Hz), 6.49 (1H, d, J=8 Hz), 6.66 (1H, t, J=8 Hz), 7.1–7.8 (20H, m)

PREPARATION 48

2-(N,N-Diphenylcarbamoyloxymethyl)-5-t-butyldiphenylsilyloxy-3,4-dihydronaphthalene was prepared from 2-ethoxycarbonyl-5-t-butyldiphenylsilyloxy-3,4-dihydronaphthalene in similar manners to those of Preparations 13 and 46.

IR (neat): 1710 cm$^{-1}$; NMR (CDCl$_3$, δ): 1.10 (9H, m), 2.23 (2H, t, J=8.4 Hz), 2.97 (2H, t, J=8.4 Hz), 4.77 (2H, s), 6.23 (1H, s), 6.31 (1H, d, J=8 Hz), 6.50 (1H, d, J=6.8 Hz), 6.68 (1H, t, J=8 Hz), 7.2–7.8 (20H, m);

PREPARATION 49

2-(N,N-Diphenylcarbamoyloxymethyl)-2-methyl-5-methoxy-1,2,3,4-tetrahydronaphthalene was prepared from 2-methoxycarbonyl-2-methyl-5-methoxy-1,2,3,4-tetrahydronaphthalene in similar manners to those of Preparations 1 and 46.

IR (neat): 1700 cm$^{-1}$; NMR (CDCl$_3$, δ): 0.83 (3H, s), 1.4 (2H, m), 2.2–2.8 (4H, m), 3.80 (3H, m), 3.90 (1H, d, J=10.4 Hz), 4.00 (1H, d, J=10.4 Hz), 6.59 (1H, d, J=8 Hz), 6.63 (1H, d, J=8 Hz), 7.08 (1H, t, J=8 Hz), 7.1–7.5 (10H, m); MS m/z: 402 (M$^+$+1)

PREPARATION 50

1-[2-(N,N-Diphenylcarbamoyloxy)ethyl]-1-hydroxy-5-t-butyldiphenylsilyloxy-1,2,3,4-tetrahydronaphthalene was prepared from 1-ethoxycarbonylmethyl-1-hydroxy-5-t-butyldiphenylsilyloxy-1,2,3,4-tetrahydronaphthalene in similar manners to those of Preparations 1 and 46.

IR (neat): 3450, 1710 cm$^{-1}$; NMR (CDCl$_3$, δ): 1.09 (9H, s), 1.6–2.2 (6H, m), 2.7–3.0 (2H, m), 4.33 (2H, t, J=6.6 Hz), 6.26 (1H, d, J=8 Hz), 6.78 (1H, t, J=8 Hz), 6.96 (1H, d, J=8 Hz), 7.1–7.8 (20H, m); MS m/z: 626 (M$^+$−17)

PREPARATION 51

5-t-Butyldiphenylsilyloxy-1,2-dihydroxy-1-[2-(N,N-diphenylcarbamoyloxy)ethyl]-1,2,3,4-tetrahydronaphthalene was prepared from 5-t-butyldiphenylsilyloxy-1-[2-(N,N-diphenylcarbamoyloxy)ethyl]-3,4-dihydronaphthalene in a similar manner to that of Example 21.

IR (neat): 3500–3400, 1700 cm$^{-1}$; NMR (CDCl$_3$, δ): 1.09 (9H, m), 1.7–2.2 (4H, m), 2.6–3.1 (2H, m), 3.8–4.0 (1H, m), 4.1–4.4 (2H, m), 6.32 (1H, d, J=8 Hz), 6.77 (1H, t, J=8 Hz), 7.01 (1H, d, J=8 Hz), 7.1–7.8 (20H, m);

PREPARATION 52

A solution of 5-t-butyldiphenylsilyloxy-1,2-dihydroxy-1-[2-(N,N-diphenylcarbamoyloxy)ethyl]-1,2,3,4-tetrahydronaphthalene (2.0 g) and p-toluenesulfonic acid (20 mg) in toluene (40 ml) was stirred for 30 minutes under reflux. The mixture was washed with 1N-HCl solution, sat. NaHCO$_3$, and brine, dried over MgSO$_4$, and evaporated in vacuo. The residue was purified by chromatography on silica gel to afford 5-t-butyl-diphenylsilyloxy-1-[2-(N,N-diphenylcarbamoyloxy)ethyl]-2-oxo-1,2,3,4-tetrahydronaphthalene (1.0 g).

IR (neat): 1800, 1705 cm$^{-1}$; NMR (CDCl$_3$, δ): 1.12 (9H, s), 2.0–2.6 (4H, m), 2.7–3.0 (1H, m), 3.1–3.4 (2H, m), 4.0–4.2 (2H, m), 6.40 (1H, d, J=8 Hz), 6.48 (1H, d, J=8 Hz), 6.76 (1H, t, J=8 Hz), 7.1–7.8 (20H, m); MS m/z: 638 (M$^+$+1)

PREPARATION 53

To a solution of 5-t-butyldiphenylsilyloxy-1-[2-(N,N-diphenylcarbamoyloxy)ethyl]-2-oxo-1,2,3,4-tetrahydronaphthalene (0.9 g) in THF (tetrahydrofuran) (20 ml) was added methylmagnesium bromide (2.0 ml, 1M solution in THF) at 0° C. under N$_2$. After being stirred for 1 hour at the room temperature, the solution was poured into a mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 5-t-butyldiphenylsilyloxy-1-[2-(N,N-diphenylcarbamoyloxy)ethyl]-2-hydroxy-2-methyl-1,2,3,4-tetrahydronaphthalene (0.6 g).

IR (neat): 3400, 1705 cm$^{-1}$; NMR (CDCl$_3$, δ): 1.11 (9H, s), 1.22 (3H, s), 1.6–2.6 (5H, m), 2.6–3.2 (2H, m), 4.0–4.4 (2H, m), 6.27 (1H, d, J=8 Hz), 6.39 (1H, d, J=8 Hz), 6.65 (1H, t, J=8 Hz), 7.1–7.8 (20H, m); MS m/z: 638 (M$^-$−18)

PREPARATION 54

To a solution of 1-[2-(N,N-diphenylcarbamoyloxy)-ethyl]-5-t-butyldiphenylsilyloxy-3,4-dihydronaphthalene (2.0 g) in THF (tetrahydrofuran) (20 ml) was added BH$_3$ (4.8 ml, 1M solution in THF) at 0° C. under N$_2$. After being stirred for 12 hours at the room temperature, 2N-NaOH solution (1.5 ml) and H$_2$O$_2$ (1.0 ml, 35% solution) were added to the solution and stirred for 4 hours. The mixture was poured into a mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford (trans)-1-[2-(N,N-diphenylcarbamoyl-oxy)ethyl]-2-hydroxy-5-t-butyldiphenylsilyloxy-1,2,3,4-tetrahydronaphthalene (1.1 g).

IR (neat): 3400, 1700 cm$^{-1}$; NMR (CDCl$_3$, δ): 1.10 (9H, s), 1.7–2.1 (4H, m), 2.7–3.0 (3H, m), 3.9–4.0 (1H, m), 4.1–4.3 (2H, m), 6.24 (1H, d, J=8 Hz), 6.49 (1H, d, J=8 Hz), 6.67 (1H, t, J=8 Hz), 7.1–7.8 (20H, m); MS m/z: 642 (M$^+$+1)

PREPARATION 55

A solution of methyl [5-methoxy-1-oxo-1,2,3,4-tetrahydro-2-naphthyl]formate (2.50 g), D-10-camphorsulfonic acid (124 mg), [RuCl$_2$(S)-binap]$_2$NEt$_3$ (90 mg) [cf. Tetrahedron Letters, Vol. 35, No. 26, pp 4559–4562, 1994], ethyl acetate (23.8 ml) and methanol (1.25 ml) was stirred under hydrogen (90 atm) at 50° C. for 40 hours. The reaction mixture was evaporated in vacuo and the residue was purified by silica gel column chromatography (n-hexane:ethyl acetate=4:1) to give (1R,2S)-methyl [1-hydroxy-5-methoxy-1,2,3,4-tetrahydro-2-naphthyl]formate (2.47 g) as a white powder.

mp: 87°–88° C.;

EXAMPLE 9

The following compounds were obtained according to a similar manner to that of Example 7.

(1) (S)-2-[(1,2,3,4-Tetrahydro-5-ethoxycarbonylmethoxy-2-naphthyl)methyl]-6-diphenylmethyl-3(2H)-pyridazinone

[α]$_D^{26}$=–20.63° (C=0.95, CH$_2$Cl$_2$); IR (Film): 1750, 1660, 1580, 760, 720, 700 cm$^{-1}$; NMR (CDCl$_3$, δ): 1.35–1.60 (1H, m), 1.29 (3H, t, J=7.1 Hz), 1.80–2.00 (1H, m), 2.20–3.20 (5H, m), 4.15–4.20 (2H, m), 4.25 (2H, q, J=7.1 Hz), 4.61 (2H, s), 5.45 (1H, s), 6.51 (1H, d, J=7.8 Hz), 6.64 (1H, d, J=7.8 Hz), 6.86 (1H, d, J=9.5 Hz), 7.08 (1H, dd, J=7.8 Hz, 7.8 Hz), 7.10–7.35 (11H, m)

(2) 2-[(3,4-Dihydro-5-ethoxycarbonylmethoxy-2-naphthyl)methyl]-6-diphenylmethyl-3(2H)-pyridazinone IR (Film): 1740, 1660, 1600 cm$^{-1}$; NMR (CDCl$_3$, δ): 1.30 (3H, t, J=7.1 Hz), 2.23 (2H, t, J=8.3 Hz), 2.86 (2H, t, J=8.3 Hz), 4.26 (2H, q, J=7.1 Hz), 4.62 (2H, s), 4.84 (2H, s), 5.44 (1H, s), 6.26 (1H, s), 6.50–6.70 (2H, m), 6.85–6.90 (1H, m), 7.00–7.35 (12H, m); MASS (+APCI): 507 (M$^+$+1)

(3) 1-[(3,4-Dihydro-5-ethoxycarbonylmethoxy-2-naphthyl)methyl]-5-diphenylmethyl-2(1H)-pyridone IR (Film): 1750, 1660, 1600 cm$^{-1}$; NMR (CDCl$_3$, δ): 1.30 (3H, t, J=7.1 Hz), 2.17 (2H, t, J=8.1 Hz), 2.85 (2H, t, J=8.1 Hz), 4.27 (2H, q, J=7.1 Hz), 4.62 (2H, s), 5.23 (1H, s), 6.14 (1H, s), 6.50–6.70 (3H, m), 6.80–6.85 (1H, m), 7.05–7.35 (12H, m); MASS (+APCI): 506 (M$^+$+1)

(4) 1-[(3,4-Dihydro-5-ethoxycarbonylmethoxy-2-naphthyl)methyl]-3-diphenylmethyl-2(1H)-yridone IR (Film): 1750, 1660, 1600 cm$^{-1}$; NMR (CDCl$_3$, δ): 1.29 (3H, t, J=7.1 Hz), 2.20 (2H, J=8.6 Hz), 2.89 (2H, t, J=8.6 Hz), 4.25 (2H, q, J=7.1 Hz), 4.61 (2H, s), 4.71 (2H, s), 5.30 (1H, s), 5.82 (1H, s), 6.12 (1H, t, J=6.8 Hz), 6.60–6.70 (3H, m), 7.00–7.35 (12H, m); MASS (+APCI) 506 (M$^+$+1)

EXAMPLE 10

The following compounds were obtained according to a similar manner to that of Example 1.

(1) [1,2,3,4-Tetrahydro-5-(methoxycarbonylmethoxy)-2-naphthyl]methyl N,N-diphenylcarbamate mp: 89.5°–91° C.; IR (Nujol): 1765, 1710, 1590, 1205 cm$^{-1}$; NMR (CDCl$_3$, δ): 1.23–1.44 (1H, m), 1.86–2.01 (2H, m), 2.35–2.75 (3H, m), 2.90–2.99 (1H, m), 3.79 (3H, s), 4.07–4.23 (2H, m), 4.62 (2H, s), 6.51 (1H, d, J=8.0 Hz), 6.69 (1H, d, J=7.6 Hz), 7.03 (1H, t, J=7.8 Hz), 7.16–7.38 (10H, m); (+) APCI MS m/z: 446 (M$^+$+1)

(2) [6-or 8-Chloro-1,2,3,4-tetrahydro-5-(methoxycarbonylmethoxy)-2-naphthyl]methyl N,N-diphenylcarbamate IR (Film): 1755, 1705 cm$^{-1}$; NMR (CDCl$_3$, δ): 1.25–1.36 (1H, m), 1.8–2.05 (2H, m), 2.18–2.33 (1H, m), 2.4–2.65 (1H, m), 2.82–3.02 (2H, m), 3.79 (3H, s), 4.07–4.27 (2H, m), 4.61 (2H, s), 6.48 (1H, d, J=8.7 Hz), 7.12 (1H, d, J=8.7 Hz), 7.16–7.39 (10H, m); (+) APCI MS m/z: 480 (M$^+$+1)

(3) Benzhydryl N-[[1,2,3,4-tetrahydro-5-(methoxycarbonylmethoxy)-2-naphthyl]methyl] carbamate mp: 101°–102° C.; IR (Nujol): 3350, 3320, 1765, 1680, 250, 1215 cm$^{-1}$; NMR (CDCl$_3$, δ): 1.35–1.43 (1H, m), 1.94 (2H, m), 2.36–2.59 (2H, m), 2.78–3.03 (2H, m), 3.22 (2H, t, J=6.4 Hz), 3.79 (3H, s), 4.63 (2H, s), 4.99 (1H, m), 6.51 (1H, d, J=8.0 Hz), 6.71 (1H, d, J=7.6 Hz), 6.81 (1H, s), 7.03 (1H, t, J=7.9 Hz), 7.15–7.35 (10H, m); (+) APCI MS m/z: 167

EXAMPLE 11

To a solution of (2R)-2-hydroxy-2-(N,N-diphenylcarbamoyloxymethyl)-5-t-butyldiphenylsilyloxy-1,2,3,4-tetrahydronaphthalene (1.9 g) in THF (tetrahydrofuran) (20 ml) was added tetrabutylammonium fluoride (5 ml, 1N-THF solution). After being stirred for 1 hour at the room temperature, the solution was extracted with ethyl acetate. The mixture was washed with water and brine. The dried solvent was evaporated in vacuo. The obtained oil was dissolved into N,N-dimethylformamide (10 ml) and then K$_2$CO$_3$ (1.0 g) and ethyl bromoacetate (0.6 ml) were added at room temperature. The mixture was stirred for 2 hours at the same temperature and partitioned between ethyl acetate and water. The organic layer was washed with water, sat. NaHCO$_3$, and brine. The dried solvent was evaporated in vacuo and the residue was purified by chromatography on silica gel to give (2R)-2-hydroxy-2-(N,N-diphenylcarbamoyloxymethyl)-5-ethoxycarbonylmethoxy-1,2,3,4-tetrahydronaphthalene (1.1 g).

IR (neat): 3400, 1720, 1700 cm$^{-1}$; NMR (CDCl$_3$, δ): 1.25 (3H, t, J=7 Hz), 1.6–2.0 (2H, m), 2.6–3.0 (4H, m), 4.10 (2H, 3), 4.14 (2H, q, J=7 Hz), 4.60 (2H, s), 6.52 (1H, d, J=8 Hz), 6.66 (1H, d, J=8 Hz), 7.10 (1H, t, J=8 Hz), 7.2–7.5 (10H, m); MS m/z: 476 (M$^+$+1); HPLC: chiralcel AD, 50% ethanol/hexane, 12.8 ml/min

EXAMPLE 12

The following compounds were obtained according to a similar manner to that of Example 11.

(1) (2S)-2-Hydroxy-2-(N,N-diphenylcarbamoyloxymethyl)-5-ethoxycarbonylmethoxy-1,2,3,4-tetrahydronaphthalene HPLC: chiralcel AD, 50% ethanol/hexane, 11.7 ml/min (2) 2-(N,N-Diphenylcarbamoyloxymethyl)-5-ethoxycarbonylmethyloxy-3,4-dihydronaphthalene IR (neat): 1740, 1705 cm$^{-1}$; NMR (CDCl$_3$, δ): 1.29 (3H, t, J=7 Hz), 2.18 (2H, t, J=8.4 Hz), 2.87 (2H, t, J=8.4 Hz), 4.25 (2H, q, J=7 Hz), 4.61 (2H, s), 4.75 (2H, s), 6.25 (1H, s), 6.5–6.7 (2H, m), 7.06 (1H, t, J=8 Hz), 7.2–7.5 (10H, m)

(3) (cis)-2-(N,N-Diphenylcarbamoyloxymethyl)-5-ethoxycarbonylmethyloxy-1-hydroxy-1,2,3,4-tetrahydronaphthalene IR (neat): 3400, 1740, 1700 cm$^{-1}$; NMR (CDCl$_3$, δ): 1.25 (3H, t, J=7 Hz), 1.4–2.1 (3H, m), 2.4–3.2 (3H, m), 4.25 (2H, q, J=7 Hz), 4.4–4.7 (5H, m), 6.63 (1H, d, J=8 Hz), 6.99 (1H, d, J=8 Hz), 7.15 (1H, t, J=8 Hz), 7.2–7.5 (10H, m); MS m/z: 458 (M$^+$–17)

(4) (trans)-2-(N,N-Diphenylcarbamoyloxymethyl)-5-ethoxycarbonylmethyloxy-1-hydroxy-1,2,3,4-tetrahydronaphthalene IR (neat): 3400, 1740, 1695 cm$^{-1}$; NMR (CDCl$_3$, δ): 1.27 (3H, t, J=7 Hz), 1.4–2.1 (3H, m), 2.5–3.1 (2H, m), 4.16 (1H, m), 4.25 (2H, q, J=7 Hz), 4.47 (1H, d, J=8.4 Hz), 4.61 (2H, s), 4.63 (1H, m), 6.59 (1H, d, J=8 Hz), 7.1–7.5 (12H, m); MS m/z: 458 (M$^+$–17)

(5) 1,2-Methylene-2-(N,N-diphenylcarbamoyloxymethyl)-5-ethoxycarbonylmethyloxy-1,2,3,4-tetrahydronaphthalene IR (neat): 1700, 1740 cm$^{-1}$; NMR (CDCl$_3$, δ): 0.8–1.1 (2H, m), 1.25 (3H, t, J=7 Hz), 1.5–2.2 (3H, m), 3.1–3.3 (1H, m), 4.1–4.4 (4H, m), 4.69 (2H, s), 6.54 (1H, d, J=8 Hz), 6.85 (1H, d, J=8 Hz), 7.05 (1H, t, J=8 Hz), 7.1–7.5 (10H, m)

(6) 1,2-Methylene-1-[2-N,N-diphenylcarbamoyloxy)ethyl]-5-ethoxycarbonylmethyloxy-1,2,3,4-tetrahydronaphthalene IR (neat): 1700, 1740 cm$^{-1}$; NMR (CDCl$_3$, δ): 1.6–1.9 (2H, m), 1.25 (3H, t, J=8 Hz), 1.2–2.2 (5H, m), 2.6–3.1 (2H, m), 4.0–4.4 (4H, m), 4.60 (2H, s), 6.50 (1H, d, J=8 Hz), 7.0–7.5 (12H, m); MS m/z: 486 (M$^+$+1)

(7) 1-[2-(N,N-Diphenylcarbamoyloxy)ethyl]-2-hydroxy-2-methyl-5-ethoxycarbonylmethyloxy-1,2,3,4-tetrahydronaphthalene IR (neat): 3400, 1740, 1690 cm$^{-1}$; NMR (CDCl$_3$, δ): 1.23 (3H, s), 1.4–2.0 (4H, m), 2.2–2.8 (3H, m), 2.9–3.1 (1H, m), 4.0–4.4 (4H, m), 4.59 (2H, s), 6.52 (2H, d, J=8 Hz), 7.04 (1H, t, J=8 Hz), 7.1–7.4 (10H, m); MS m/z: 486 (M$^+$–17)

(8) (cis)-1-[2-(N,N-Diphenylcarbamoyloxy)ethyl]-2-hydroxy-5-ethoxycarbonylmethyloxy-1,2,3,4-tetrahydronaphthalene IR (neat): 3400, 1730, 1680 cm$^{-1}$; NMR (CDCl$_3$, δ): 1.25 (3H, t, J=7 Hz), 1.6–2.3 (5H, m), 2.6–3.0 (3H, m), 4.0–4.5 (5H, m), 4.61 (2H, s), 6.52 (1H, d, J=8 Hz), 6.61 (1H, d, J=8 Hz), 7.03 (1H, t, J=8 Hz), 7.1–7.4 (10H, m); MS m/z: 490 (M$^+$+1)

(9) (trans)-1-[2-(N,N-Diphenylcarbamoyloxy)ethyl]-2-hydroxy-5-ethoxycarbonylmethyloxy-1,2,3,4-tetrahydronaphthalene IR (neat): 3400, 1700–1720 cm$^1$; NMR (CDCl$_3$, δ): 1.25 (3H, t, J=7 Hz), 1.7–2.0 (4H, m), 2.6–3.0 (3H, m), 3.8–4.0 (1H, m), 4.1–4.4 (4H, m), 4.60 (2H, s), 6.52 (1H, d, J=8 Hz), 6.61 (1H, d, J=8 Hz), 7.04 (1H, t, J=8 Hz), 7.1–7.4 (10H, m); MS m/z: 490 (M$^+$+1)

(10) 1-[2-(N,N-Diphenylcarbamoyloxy)ethyl]-1-hydroxy-5-ethoxycarbonylmethyloxy-1,2,3,4-tetrahydronaphthalene IR (neat): 3450, 1720, 1705 cm$^{-1}$; NMR (CDCl$_3$, δ): 1.25 (3H, t, J=7 Hz), 1.6–2.2 (6H, m), 2.8–3.0 (2H, m), 3.7–3.9 (2H, m), 4.1–4.4 (2H, m), 4.60 (2H, s), 6.5–6.9 (2H, m), 6.96 (1H, d, J=8 Hz), 7.1–7.4 (10H, m); MS m/z: 472 (M+–17)

(11) 1-[2-(N,N-Diphenylcarbamoyloxy)ethyl]-5-ethoxycarbonylmethyloxy-3,4-dihydronaphthalene IR (neat): 1740, 1705 cm$^{-1}$; NMR (CDCl$_3$, δ): 1.25 (3H, t, J=7 Hz), 2.1 (2H, m), 2.7–2.9 (4H, m), 4.2–4.4 (4H, m), 4.61 (2H, s), 5.79 (1H, t, J=4.4 Hz), 6.59 (1H, d, J=8 Hz), 6.94 (1H, d, J=8 Hz), 7.01 (1H, t, J=8 Hz), 7.1–7.4 (10H, m)

EXAMPLE 13

To a methylene chloride solution (10 ml) of 2-[2-(5-methoxy-1,2,3,4-tetrahydro-1-naphthyl)ethyl]-6-diphenylmethyl-3(2H)-pyridazinone (0.25 g) was added a methylene chloride solution of boron tribromide (1N, 0.78 ml) at –5° C., and the solution was stirred at the same temperature for 4 hours. The reaction mixture was washed with water and brine, dried over sodium sulfate, and evaporated in vacuo. The residue was crude 2-[2-(5-hydroxy-1,2,3,4-tetrahydro-1-naphthyl)ethyl]-6-diphenylmethyl-3(2H)-pyridazinone (0.34 g).

A N,N-dimethylformamide solution (15 ml) of crude 2-[2-(5-hydroxy-1,2,3,4-tetrahydro-1-naphthyl)ethyl]-6-diphenylmethyl-3(2H)-pyridazinone (0.34 g), potassium carbonate (0.16 g) and ethyl bromoacetate (0.2 ml) was stirred at room temperature for 24 hours. The reaction mixture was partitioned between ethyl acetate and water. The organic layer was washed with water and brine, dried over sodium sulfate, and evaporated in vacuo. The residue was chromatographed (n-hexane-ethyl acetate=3:2) over silica gel to afford 2-[2-(5-ethoxycarbonylmethoxy-1,2,3,4-tetrahydro-1-naphthyl)ethyl]-6-diphenylmethyl-3(2H)-pyridazinone (0.17 g) as a pale yellow oil.

IR (CH$_2$Cl$_2$ solution): 1750, 1660, 1585 cm$^{-1}$; NMR (CDCl$_3$, δ): 1.50–2.02 (6H, m), 2.04–2.58 (1H, m), 2.80–2.95 (2H, m), 4.10–4.31 (4H, m), 4.60 (2H, s), 5.45 (1H, s), 6.50 (1H, d, J=7.9 Hz), 6.72 (1H, d, J=7.9 Hz), 6.84 (1H, d, J=9.5 Hz) 6.97–7.54 (12H, m); MASS (APCI) m/z: 523 (M$^+$+1)

EXAMPLE 14

The following compound was obtained according to a similar manner to that of Example 13.

2-(N,N-Diphenylcarbamoyloxymethyl)-2-methyl-5-ethoxycarbonylmethyloxy-1,2,3,4-tetrahydronaphthalene IR (neat): 1740, 1700 cm$^{-1}$; NMR (CDCl$_3$, δ): 0.83 (3H, s), 1.25 (3H, t, J=7 Hz), 1.52 (2H, m), 2.2–2.9 (4H, m), 3.92 (1H, d, J=10.2 Hz), 4.00 (1H, d, J=10.2 Hz), 4.24 (2H, q, J=7 Hz), 4.60 (2H, s), 6.50 (1H, d, J=8 Hz), 6.64 (1H, d, J=8 Hz), 7.06 (1H, t, J=8 Hz), 7.2–7.5 (10H, m); MS m/z: 474 (M$^+$+1)

EXAMPLE 15

To a solution of 2-(N,N-Diphenylcarbamoyloxymethyl)-5-t-butyldiphenylsilyloxy-1,2,3,4-tetrahydronaphthalene (1.3 g) in CH$_2$Cl$_2$ (30 ml) were added Na$_2$CO$_3$ (290 mg) and m-chloroperbenzoic acid (550 mg) at 0° C. After being stirred for 2 hours, the solvent was removed in vacuo.

The residue was extracted with ethyl acetate. The mixture was washed with 1N-HCl solution, sat. NaHCO$_3$, and brine, dried over MgSO$_4$, and evaporated in vacuo. The residue was purified by chromatography on silica gel to afford 1,2-epoxy-2-(N,N-diphenylcarbamoyloxymethyl)-5-t-butyldiphenylsilyloxy-1,2,3,4-tetrahydronaphthalene. This compound was treated in a similar manner to that of Example 11 to give 1,2-epoxy-2-(N,N-diphenylcarbamoyloxymethyl)-5-ethoxycarbonylmethyloxy-1,2,3,4-tetrahydronaphthalene (370 mg).

IR (neat): 1720 cm$^{-1}$; NMR (CDCl$_3$, δ): 1.25 (3H, t, J=7 Hz), 1.6–1.9 (1H, m), 2.1–2.5 (2H, m), 3.0–3.2 (1H, m), 3.59 (1H, m), 4.23 (2H, q, J=7 Hz), 4.58 (2H, s), 6.73 (1H, d, J=8 Hz), 6.93 (1H, d, J=8 Hz), 7.08 (1H, t, J=8 Hz), 7.1–7.7 (10H, m); MS m/z: 474 (M$^+$+1)

EXAMPLE 16

To a solution of 5-t-butyldiphenylsilyloxy-1-[2-(N,N-diphenylcarbamoyloxy)ethyl]-2-hydroxy-2-methyl-1,2,3,4- tetrahydronaphthalene (800 mg) in toluene (20 ml) was added KHSO$_4$ (100 mg). The mixture was stirred for 1 hour under reflux, and then the cooled solution was washed with sat. NaHCO$_3$ and brine. The dried solvent was evaporated in vacuo and the residue was dissolved in THF (tetrahydrofuran) (20 ml). To the solution was added tetrabutylammonium fluoride (2 ml, 1N-THF solution). After being stirred for 1 hour at the room temperature, the solution was extracted with ethyl acetate. The mixture was washed with water and brine. The dried solvent was evaporated in vacuo. The obtained oil was dissolved into N,N-dimethylformamide (5 ml) and ethyl bromoacetate (0.2 ml) was added thereto at room temperature. The mixture was stirred for 2 hours at the same temperature and partitioned between ethyl acetate and water. The organic layer was washed with water, sat. NaHCO$_3$, and brine. The dried solvent was evaporated in vacuo and the residue was purified by chromatography on silica gel to give 1-[2-(N,N-diphenylcarbamoyloxy)ethyl]-2-methyl-5-ethoxycarbonylmethyloxy-3,4-dihydronaphthalene (310 mg).

IR (neat): 740, 1700 cm$^{-1}$; NMR (CDCl$_3$, δ): 1.25 (3H, t, J=8 Hz), 1.89 (3H, s), 1.9–2.2 (1H, m), 2.8–3.3 (3H, m), 3.42 (1H, m), 3.8–4.1 (1H, m), 4.1–4.4 (4H, m), 4.62 (2H, s) 6.54 (1H, d, J=8 Hz), 6.62 (1H, d, J=8 Hz), 7.07 (1H, t, J=8 Hz), 7.1–7.5 (10H, m); MS m/z: 486 (M$^+$+1)

EXAMPLE 17

A mixture of ethyl [5,6,7,8-tetrahydro-6-(2-hydroxyethyl)-1-naphthyloxy]acetate (50 mg), N,N-diphenylcarbamoyl chloride (50 mg), and pyridine (32 mg) was stirred at 100° C. for 1 hour and 40 minutes, cooled to room temperature, and partitioned between ethyl acetate and 1N hydrochloric acid. The ethyl acetate layer was washed successively with water, aqueous sodium bicarbonate, and brine, dried over magnesium sulfate, and evaporated in vacuo. The residue was chromatographed (toluene-ethyl acetate) over silica gel to afford 2-[5-(ethoxycarbonylmethoxy)-1,2,3,4-tetrahydro-2-naphthyl]ethyl N,N-diphenylcarbamate (31 mg) as a syrup.

IR (Film): 1755, 1705, 1195 cm$^{-1}$; NMR (CDCl$_3$, δ): 1.30 (3H, t, J=7.1 Hz), 1.25–1.42 (1H, m), 1.61–1.70 (3H, m), 1.86–1.93 (1H, m), 2.29–2.64 (2H, m), 2.71–2.97 (2H, m), 4.20–4.32 (4H, m), 4.61 (2H, s), 6.51 (1H, d, J=8.0 Hz), 6.67 (1H, d, J=7.6 Hz), 7.03 (1H, t, J=7.9 Hz), 7.13–7.36 (10H, m); (+) APCI MS m/z: 474 (M$^+$+1), 261

EXAMPLE 18

To a methylene chloride solution (1 ml) of phosgene dimer (0.027 ml) was added a methylene chloride solution (2 ml) of (5-ethoxycarbonylmethoxy-1,2,3,4-tetrahydro-1-naphthyl)methanol (0.12 g) and pyridine (0.1 ml) at −5° C., and the solution was stirred at room temperature for two hours. To the reaction mixture was added a solution of 1,1-diphenylhydrazine hydrochloride (0.10 g) and pyridine (0.05 ml) in methylene chloride (2 ml). The solution was stirred at room temperature for 3 hours, washed with 5% hydrochloric acid, water, and brine, dried over sodium sulfate, and evaporated in vacuo. The residue was chromatographed (n-hexane-ethyl acetate) over silica gel to afford 2-[(5-ethoxycarbonylmethoxy-1,2,3,4-tetrahydro-1-naphthyl)methoxycarbonyl]-1,1-diphenyihydrazine (0.13 g) as colorless solids.

NMR (CDCl$_3$, δ): 1.29 (3H, t, J=7.1 Hz), 1.65–2.00 (3H, m), 2.44–3.32 (4H, m), 4.25 (2H, q, J=7.1 Hz), 4.15–4.44 (2H m), 4.62 (2H, s), 6.56 (1H, d, J=7.8 Hz), 6.65–7.20 (8H, m), 7.20–7.40 (5H, m); MASS (APCI) m/z: 475 (M$^+$+1)

EXAMPLE 19

A solution of ethyl (6-amino-5,6,7,8-tetrahydro-1-naphthyloxy)acetate (83 mg) and 4-nitrophenyl(benzhydryl)carbonate (116 mg) in N,N-dimethylformamide (2 ml) was stirred at 50° C. for 1 hour and 30 minutes, cooled to room temperature, and extracted with ethyl acetate. The extract was washed five times with aqueous sodium bicarbonate and with brine, dried over sodium sulfate, and evaporated in vacuo. The residue was chromatographed (toluene-ethyl acetate) over silica gel to afford benzhydryl N-[1,2,3,4-tetrahydro-5-(ethoxycarbonylmethoxy)-2-naphthyl]carbamate (110 mg) as an oil.

IR (Film): 1750, 1720, 1705, 1210 cm$^{-1}$; NMR (CDCl$_3$, δ): 1.29 (3H, t, J=7.1 Hz), 1.79 (1H, m), 2.04 (1H, m), 2.65 (1H, dd, J=16.4, 8.0 Hz), 2.79–2.89 (2H, m), 3.11 (1H, dd, J=16.3, 4.5 Hz), 4.04 (1H, m), 4.26 (2H, q, J=7.1 Hz), 4.62 (2H, s), 4.91 (1H, br d), 6.54 (1H, d, J=8.1 Hz), 6.71 (1H, d, J=7.6 Hz), 6.81 (1H, s), 7.06 (1H, t, J=7.9 Hz), 7.15–7.35 (10H, m); (+) APCI MS m/z: 167

EXAMPLE 20

60% Sodium hydride (10.2 mg) was added to a stirred solution of benzhydryl N-[[1,2,3,4-tetrahydro-5-(methoxycarbonylmethoxy)-2-naphthyl]methyl]carbamate (117 mg) and methyl iodide (36 mg) in N,N-dimethylformamide (1.2 ml) under ice cooling and the mixture was stirred at the same temperature for 7 hours, then another 60% sodium hydride (10.2 mg) and methyl iodide (36 mg) was added thereto. The resulting mixture was stirred at room temperature for 3 days and extracted with ethyl acetate. The extract was washed twice with brine, dried over magnesium sulfate, and evaporated in vacuo. The residue was chromatographed (toluene-ethyl acetate) over silica gel to afford benzhydryl N-methyl-N-[[1,2,3,4-tetrahydro-5-(methoxycarbonylmethoxy)-2-naphthyl]methyl]carbamate (71 mg) as an oil.

IR (Film): 1755, 1730 (shoulder), 1690, 1200 cm$^{-1}$; NMR (CDCl$_3$, δ): 1.25–1.45 (1H, m), 1.85–2.15 (2H, m), 2.35–2.8 (3H, m), 2.96 and 3.08 (3H, s), 3.05 (1H, m), 3.3–3.5 (2H), 3.79 (3H, s), 4.63 (2H), 6.51 (1H, d, J=7.9 Hz), 6.66 (1H, m), 6.82 (1H, s), 7.03 (1H, m), 7.18–7.33 (10H, m); (+) APCI MS m/z: 167

EXAMPLE 21

To a solution of 2-(N,N-diphenylcarbamoyloxymethyl)-5-ethoxycarbonylmethyloxy-3,4-dihydronaphthalene (270 mg) in a mixture of acetonitrile (10 ml) and water (5 ml) were added 4-methylmorphorine N-oxide (0.34 ml) and OSO$_4$ (1 ml, 2.5% in t-butyl alcohol) at 0° C. After being stirred for 4 hours, the solution was diluted into ethyl acetate. The mixture was washed with 1N-HCl solution, sat. NaHCO$_3$, and brine, dried over MgSO$_4$, and evaporated in vacuo. The residue was purified by chromatography on silica gel to afford 1,2-dihydroxy-2-(N,N-diphenylcarbamoyloxymethyl)-5-ethoxycarbonylmethyloxy-1,2,3,4-tetrahydronaphthalene.

IR (neat): 3400, 1720 cm$^{-1}$; NMR (CDCl$_3$, δ): 1.29 (3H, t, J=7 Hz), 1.6–2.2 (2H, m), 2.6–3.2 (4H, m), 4.25 (2H, q, J=7 Hz), 4.4–4.6 (3H, m), 4.61 (2H, s), 6.61 (1H, m), 7.1–7.6 (12H, m); MS m/z: 474 (M$^+$−17)

EXAMPLE 22

The following compound was obtained according to a similar manner to that of Example 21.

1-[2-(N,N-Diphenylcarbamoyloxy)ethyl]-1,2-dihydroxy-5-ethoxycarbonylmethyloxy-1,2,3,4-tetrahydronaphthalene IR (neat): 3450, 1740, 1705 cm$^{-1}$; NMR (CDCl$_3$, δ): 1.25 (3H, t, J=7 Hz), 1.7–2.2 (4H, m), 2.6–3.0 (2H, m), 3.82 (1H, m), 4.2–4.4 (4H, m), 4.59 (2H, s), 6.50 (1H, m), 7.1–7.4 (12H, m); MS m/z: 488 (M$^+$–17)

EXAMPLE 23

To a solution of 1,2-epoxy-2-(N,N-diphenylcarbamoyloxymethyl)-5-ethoxycarbonylmethyloxy-1,2,3,4-tetrahydronaphthalene (0.2 g) in CH$_2$Cl$_2$ (30 ml) was added HF-pyridine (0.5 ml) at 0° C. After being stirred for 2 hours, the solvent was removed in vacuo. The residue was extracted with ethyl acetate. The mixture was washed with 1N-HCl solution, sat. NaHCO$_3$, and brine, dried over MgSO$_4$, and evaporated in vacuo. The residue was purified by chromatography on silica gel to afford 1-fluoro-2-hydroxy-2-(N,N-diphenylcarbamoyloxymethyl)-5-ethoxycarbonylmethyloxy-1,2,3,4-tetrahydronaphthalene (70 mg)

IR (neat): 1700 cm$^{-1}$; NMR (CDCl$_3$, δ): 1.26 (3H, t, J=7 Hz), 1.5–2.1 (4H, m), 2.6–3.0 (2H, m), 4.0–4.5 (4H, m), 4.62 (2H, m), 5.20 (1H, d, J=52 Hz), 6.69 (1H, m), 7.0–7.5 (12H, m); MS m/z: 494 (M$^+$+1)

EXAMPLE 24

To a solution of 2-hydroxy-2-(N,N-diphenylcarbamoyloxymethyl)-5-ethoxycarbonylmethyloxy-1,2,3,4-tetrahydronaphthalene (100 mg) in CH$_2$Cl$_2$ (10 ml) was added diethylaminosulfur trifluoride (0.5 ml) at –78° C. After being stirred for 30 minutes, the mixture was washed with sat. NaHCO$_3$ and brine, dried over MgSO$_4$, and evaporated in vacuo. The residue was purified by chromatography on silica gel to afford 2-fluoro-2-(N,N-diphenylcarbamoyloxymethyl)-5-ethoxycarbonylmethyloxy-1,2,3,4-tetrahydronaphthalene (40 mg).

NMR (CDCl$_3$, δ): 1.25 (3H, d, J=7 Hz), 1.6–2.0 (2H, m), 2.8–3.0 (4H, m), 4.26 (2H, q, J=7 Hz), 4.27 (2H, d, J=22 Hz), 4.76 (2H, s), 6.54 (1H, d, J=8 Hz), 6.64 (1H, d, J=8 Hz), 7.06 (1H, t, J=8 Hz), 7.1–7.5 (10H, m); MS m/z: 478 (M$^+$+1)

EXAMPLE 25

The following compound was obtained according to a similar manner to that of Example 24.

1-[2-(N,N-Diphenylcarbamoyloxy)ethyl]-2-fluoro-5-ethoxycarbonylmethyloxy-1,2,3,4-tetrahydronaphthalene NMR (CDCl$_3$, δ): 1.25 (3H, t, J=7 Hz), 1.7–2.1 (4H, m), 2.6–2.9 (2H, m), 4.1–4.4 (4H, m), 4.60 (2H, s), 6.5–6.7 (2H, m), 7.0–7.4 (11H, m); MS m/z: 492 (M$^+$+1)

EXAMPLE 26

A solution of 2-[(3,4-dihydro-5-ethoxycarbonylmethoxy-2-naphthyl)methyl]-6-diphenylmethyl-3(2H)-pyridazinone (0.20 g) and 3-chloroperoxybenzoic acid (94 mg) in dichloromethane (5 ml) was allowed to stand in a freezer (about –15° C.) for overnight. The reaction mixture was evaporated in vacuo and the residue was partitioned between ethyl acetate and sodium hydrogencarbonate solution. The organic layer was separated and washed with water, brine, dried over magnesium sulfate and evaporated in vacuo. The residue and 10% palladium on carbon in ethyl acetate (5 ml) and acetic acid (one drop) were stirred under hydrogen (1 atm) at room temperature for 4 hours. The catalyst was filtered off and the filtrate was evaporated in vacuo. The residue was purified by silica gel column chromatography (n-hexane-ethyl acetate=2:1~1:1) to give 2-[(1,2,3,4-tetrahydro-5-ethoxycarbonylmethoxy-2-hydroxy-2-naphthyl)methyl]-6-diphenylmethyl-3(2H)-pyridazinone (0.08 g) as a pale yellow oil.

IR (CH$_2$Cl$_2$): 3600–3100, 1750, 1660 cm$^{-1}$; NMR (CDCl$_3$, δ): 1.29 (3H, t, J=7.1 Hz), 1.60–2.00 (2H, m), 2.75–3.00 (4H, m), 4.20–4.35 (4H, m), 4.61 (2H, s), 5.43 (1H, s), 6.53 (1H, d, J=8 Hz), 6.61 (1H, d, J=8 Hz), 6.90–7.35 (13H, m); MASS (+APCI): 525 (M$^+$+1)

EXAMPLE 27

A solution of 2-[(5-ethoxycarbonylmethoxy-1,2,3,4-tetrahydro-1-naphthyl)methoxycarbonyl]-1,1-diphenylhydrazine (0.17 g) and 1N-aqueous sodium hydroxide (1 ml) in dioxane (1.5 ml) was stirred at room temperature for 30 minutes and partitioned between 5% hydrochloric acid and ethyl acetate. The organic layer was washed with brine, dried over sodium sulfate, and evaporated in vacuo. The residue was washed with isopropanol to afford 2-[(5-carboxymethoxy-1,2,3,4-tetrahydro-1-naphthyl)-methoxycarbonyl]-1,1-diphenylhydrazine (0.08 g) as a colorless powder.

IR (Nujol): 3230, 1730, 1700 cm$^{-1}$; NMR (CD$_3$OD, δ): 1.49–2.01 (4H, m), 2.70–3.13 (3H, m), 4.10–4.47 (2H, m), 4.48 (2H, s), 6.62–7.30 (14H, m); MASS (APCI) m/z: 447 (M$^+$+1)

EXAMPLE 28

The following compounds were obtained according to similar manners to those of Examples 3, 4 and 8.

(1) (S)-2-[(1,2,3,4-Tetrahydro-5-carboxymethoxy-2-naphthyl)methyl]-6-diphenylmethyl-3(2H)-pyridazinone

[α]$_D^{25}$=–27.6° (C=0.75, CH$_2$Cl$_2$); mp: 144°–145° C.; IR (Nujol): 2600–2200, 1740, 1640, 770, 700 cm$^{-1}$; NMR (DMSO-d$_6$, δ): 1.20–1.45 (1H, m), 1.70–1.90 (1H, m), 2.10–2.90 (5H, m), 3.90–4.10 (2H, m), 4.65 (2H, s), 5.57 (1H, s), 6.55–6.65 (2H, m), 6.90–7.05 (2H, m), 7.20–7.35 (11H, m), 12.96 (1H, br s); MASS (+APCI): 481 (M$^+$+1)

(2) 2-[(3,4-Dihydro-5-carboxymethoxy-2-naphthyl) methyl]-6-diphenylmethyl-3(2H)-pyridazinone mp: 156°–158° C.; IR (Nujol): 1710, 1630 cm$^{-1}$; NMR (DMSO-d$_6$, δ): 2.12 (2H, t, J=8.9 Hz), 2.67 (2H, t, J=8.9 Hz), 4.66 (2H, s), 4.74 (2H, s), 5.56 (1H, s), 6.13 (1H, s), 6.62 (1H, d, J=7.9 Hz), 6.71 (1H, d, J=7.9 Hz), 6.95 (1H, d, J=9.6 Hz) 7.05 (1H, d, J=7.9 Hz), 7.15–7.40 (11H, m), 13.0 (1H, br s); MASS (+APCI): 479 (M$^+$+1)

(3) 2-[(1,2,3,4-Tetrahydro-5-carboxymethoxy-2-hydroxy-2-naphthyl)methyl]-6-diphenylmethyl-3(2H)-pyridazinone mp: 122°–123° C.; IR (Nujol): 3600–3200, 1730, 1650 cm$^{-1}$; NMR (CDCl$_3$, δ): 1.50–1.90 (2H, m), 2.50–3.00 (4H, m), 3.82 (2H, br s), 4.23 (1H, d, J=13.9 Hz), 4.37 (1H, d, J=13.9 Hz), 4.63 (2H, s), 5.44 (1H, s), 6.50–6.65 (2H, m), 6.95–7.40 (13H, m); MASS (+APCI): 497 (M$^+$+1)

(4) 1-[(3,4-Dihydro-5-carboxymethoxy-2-naphthyl) methyl]-5-diphenylmethyl-2(1H)-pyridone mp: 181°–182° C.; IR (Nujol): 1730, 1650 cm$^{-1}$; NMR (DMSO-d$_6$, δ): 2.11 (2H, t, J=8.3 Hz), 2.72 (2H, t, J=8.3 Hz), 4.61 (2H, s), 4.69 (2H, s), 5.41 (1H, s), 6.03 (1H, s), 6.43 (1H, d, J=10.2 Hz), 6.60 (1H, d, J=7.4 Hz), 6.72 (1H, d, J=8.0 Hz), 7.00–7.35 (13H, m), 12.98 (1H, br s); MASS (+APCI) 478 (M$^+$+1)

(5) 1-[(3,4-Dihydro-5-carboxymethoxy-2-naphthyl) methyl]-3-diphenylmethyl-2(1H)-pyridone mp: 186°–188° C.; IR (Nujol): 1750, 1640 cm$^{-1}$; NMR (DMSO-d$_6$, δ): 2.13 (2H, t, J=8.2 Hz), 2.74 (2H, t, J=8.2 Hz), 4.66 (2H, s), 5.65 (1H, s), 5.99 (1H, s), 6.25 (1H, t, J=6.8 Hz), 6.59 (1H, d, J=7.3 Hz), 6.71 (1H, d, J=8.0 Hz), 6.87 (1H, d, J=6.7 Hz), 7.00–7.35 (11H, m), 7.59 (1H, d, J=6.7 Hz)

(6) 2-[2-(5-Carboxymethoxy-1,2,3,4-tetrahydro-1-naphthyl)ethyl]-6-diphenylmethyl-3(2H)-pyridazinone NMR (CD$_3$OD, δ): 1.60–2.25 (6H, m), 2.55–2.90 (3H, m), 4.11–4.29 (2H, m), 4.47 (2H, s), 5.55 (1H, s), 6.54–6.61 (2H, m), 6.88–6.90 (2H, m), 7.17–7.35 (11H, m); MASS (APCI) m/z: 495 (M$^+$+1)

(7) 2-[5-(Carboxymethcxy)-1,2,3,4-tetrahydro-2-naphthyl]ethyl N,N-diphenylcarbamate mp: 175°–177.5° C.; IR (Nujol): 2750–2250, 1765, 1675 cm$^{-1}$; NMR (DMSO-d$_6$, δ): 1.24 (1H, m), 1.57 (3H, m), 1.79 (1H, m), 2.2–2.5 (2H, m), 2.65–2.85 (2H, m), 4.19 (2H, m), 4.65 (2H, s), 6.56–6.64 (2H, m), 7.00 (1H, t, J=7.8 Hz), 7.18–7.39 (10H, m); (+) APCI MS m/z: 446 (M$^+$+1), 233

(8) [5-(Carboxymethoxy)-2-methyl-1,2,3,4-tetrahydro-2-naphthyl]methyl N,N-diphenylcarbamate IR (Nujol): 1700 cm$^{-1}$; NMR (CDCl$_3$, δ): 0.83 (3H, s), 1.44 (2H, m), 2.2–2.9 (4H, m), 3.92 (1H, d, J=10.6 Hz), 4.08 (1H, d, J=10.6 Hz), 4.65 (2H, s), 6.53 (1H, d, J=8 Hz), 6.66 (1H, d, J=8 Hz), 7.06 (1H, t, J=8 Hz), 7.2–7.5 (10H, m); FAB MS m/z: 446 (M$^+$+1)

EXAMPLE 29

A solution of benzhydryl N-[[1,2,3,4-tetrahydro-5-(methoxycarbonyimethoxy)-2-naphthyl]methyl]carbamate (60 mg) in a mixture of 1N sodium hydroxide aqueous solution (0.20 ml), methanol (1 ml), and 1,2-dimethoxyethane (1 ml) was stirred at room temperature for 30 minutes, neutralized with 1N hvdrochloric acid, and extracted with ethyl acetate. The extract was washed with brine, dried over magnesium sulfate, and evaporated in vacuo. The oily residue was powdered from diisopropyl ether to afford benzhydryl N-[[1,2,3,4-tetrahydro-5-(carboxymethoxy)-2-naphthyl]methyl]carbamate (51 mg) as a colorless powder.

mp: 160°–161° C.; IR (Nujol): 3350, 2800–2300, 1755, 1685 cm$^{-1}$; NMR (DMSO-d$_6$, δ): 1.2–1.35 (1H, m), 1.84 (2H, m), 2.25–2.5 (2H, m), 2.7–2.85 (2H, m), 3.01 (2H, m), 4.64 (2H, s), 6.56–6.67 (3H, m), 7.00 (1H, t, J=7.8 Hz), 7.30–7.38 (10H, m), 7.57 (1H, t), 12.9 (1H, br); (+) APCI MS m/z: 412

EXAMPLE 30

The following compound was obtained according to a similar manner to that of Example 29.

[6- or 8-Chloro-5-(carboxymethoxy)-1,2,3,4-tetrahydro-2-naphthyl]methyl N,N-diphenylcarbamate mp: 138°–144.5° C.; IR (Nujol): 2700–2300, 1740, 1710 cm$^{-1}$; NMR (DMSO-d$_6$, δ): 1.23 (1H, br m), 1.84 (2H, br m), 2.12–2.27 (1H, m), 2.35–2.6 (1H, m), 2.7–2.85 (2H, m), 4.05–4.15 (2H, m), 4.66 (2H, s), 6.69 (1H, d, J=8.8 Hz), 7.15–7.42 (11H, m); (+) APCI MS m/z: 466 (M$^+$+1)

EXAMPLE 31

To a solution of (2R)-2-hydroxy-2-(N,N-diphenylcarbamoyloxymethyl)-5-ethoxycarbonylmethoxy-1,2,3,4-tetrahydronaphthalene (0.9 g) in ethanol (20 ml) was added 1N-NaOH solution (1.9 ml). After being stirred for 4 hours at the same temperature, the solvent was removed in vacuo to give sodium salt of (2R)-[5-(carboxymethoxy)-2-hydroxy-1,2,3,4-tetrahydro-2-naphthyl]methyl N,N-diphenylcarbamate (0.9 g).

IR (Nujol): 3400, 1700, 1580 cm$^{-1}$; NMR (D$_2$O, δ): 1.2–1.6 (2H, m), 2.1–2.6 (4H, m), 3.72 (1H, d, J=11.0 Hz), 3.85 (1H, d, J=11.0 Hz), 4.13 (2H, s), 6.29 (2H, m), 6.4–7.0 (11H, m); FAB MS m/z: 470 (M$^+$+1); HPLC: chiralcel AGP, 8% acetonitrile/0.02N phosphate buffer (pH=6.0), 5.3 ml/min

EXAMPLE 32

The following compounds were obtained according to similar manners to those of Examples 6 and 31.

(1) Sodium salt of benzhydryl N-[5-(carboxymethoxy)-1,2,3,4-tetrahydro-2-naphthyl]carbamate mp: 209°–223° C. (dec.); IR (Nujol): 3340, 1695, 1615, 1250 cm$^{-1}$; NMR (DMSO-d$_6$, δ): 1.57 (1H, m), 1.94 (1H, m), 2.51–2.67 (2H, m), 2.83–2.92 (2H, m), 3.60 (1H, m), 4.10 (2H, s), 6.48–6.56 (2H, m), 6.69 (1H, s), 6.94 (1H, t, J=7.9 Hz), 7.26–7.38 (10H, m), 7.57 (1H, d, J=7.2 Hz); FAB MS m/z: 454 (M$^+$+1), 432

(2) Sodium salt of (2S)-[S-(carboxymethoxy)-2-hydroxy-1,2,3,4-tetrahydro-2-naphthyl]methyl N,N-diphenylcarbamate HPLC: chiralcel AGP, 8% acetonitrile/0.02N phosphate buffer (pH=6.0), 7.4 ml/min (3) Sodium salt of [5-(carboxvmethcxy)-3,4-dihydro-2-naphthyl]methyl N,N-diphenylcarbamate IR Nujol): 1710 cm$^{-1}$; NMR (DMSO-d$_6$, δ): 2.0–2.2 (2H, m), 2.6–2.8 (2H, m), 4.08 (2H, s), 4.68 (2H, s), 6.21 (1H, s), 6.50 (1H, d, J=8 Hz), 6.60 (1H, d, =8 Hz), 6.98 (1H, t, J=8 Hz), 7.2–7.5 (10H, m); FAB MS m/z: 452 (M$^+$+1)

(4) Sodium salt of [5-(carboxymethoxy)-1,2-dihydroxy-1,2,3,4-tetrahydro-2-naphthyl]methyl N,N-diphenylcarbamate IR (Nujol): 3400, 1650–1600 cm$^{-1}$; NMR (DMSO-d$_6$, δ): 1.6–1.8 (2H, m), 2.5–2.8 (2H, m), 4.0–4.9 (5H, s), 6.53 (1H, m), 6.9–7.5 (12H, m) FAB MS m/z: 486 (M$^+$+1)

(5) Sodium salt of [5-(carboxymethoxy)-1,2-epoxy-1,2,3,4-tetrahydro-2-naphthyl]methyl N,N-diphenylcarbamate IR (Nujol): 1700, 1590 cm$^1$; NMR (DMSO-d$_6$, δ): 1.4–1.7 (1H, m), 1.9–2.2 (2H, m), 2.8–3.1 (1H, m), 3.65 (1H, s), 4.08 (2H, s), 4.20 (1H, d, J=12.0 Hz), 4.52 (1H, d, J=12.0 Hz), 6.71 (1H, d, J=8 Hz), 6.84 (1H, d, J=8 Hz), 7.05 (1H, t, J=8 Hz), 7.2–7.5 (10H, m); FAB MS m/z: 468 (M$^+$+1)

(6) Sodium salt of (trans)-[5-(carboxymethoxy)-1-hyvdroxy-1,2,3,4-tetrahydro-2-naphthyl]methyl N,N-diphenylcarbamate IR (Nujol): 3400–3200, 1700, 1590 cm$^{-1}$; NMR (DMSO-d$_6$, δ): 1.2–1.5 (1H, m), 1.6–1.9 (2H, m), 2.2–2.8 (2H m), 4.06 (2H, s), 4.1–4.4 (3H, m), 6.52 (1H, d, J=7 Hz), 6.8–7.1 (2H, m), 7.1–7.5 (10H, m); FAB MS m/z: 470 (M$^+$+1)

(7) Sodium salt of (cis)-[5-(carboxymethoxy)-1-hydroxy-1,2,3,4-tetrahydro-2-naphthyl]methyl N,N-diphenylcarbamate IR (Nujol): 3400–3200, 1690, 1590 cm$^{-1}$; NMR (DMSO-d$_6$, δ): 1.4–2.0 (3H, m), 2.2–2.8 (2H, m), 4.10 (2H, s), 4.1–4.4 (3H, m), 6.58 (1H, d, J=8 Hz), 6.74 (1H, d, J=8 Hz), 7.00 (1H, t, J=8 Hz), 7.1–7.5 (10H, m); FAB MS m/z: 470 (M$^+$+1)

(8) Sodium salt of [5-(carboxymethoxy)-1-fluoro-2-hydroxy-1,2,3,4-tetrahydro-2-naphthyl]methyl N,N-diphenylcarbamate IR (Nujol): 3400–3300, 1710, 1600 cm$^{-1}$; NMR (DMSO-d$_6$, δ): 1.4–2.2 (2H, m), 2.5–3.2 (2H, m), 3.9–4.5 (4H, m), 5.00 (1H, d, J=52 Hz), 6.7–7.5 (13H, m); FAB MS m/z: 488 (M$^+$+1)

(9) Sodium salt of [5-(carboxymethoxy)-1,2-methylene-1,2,3,4-tetrahydro-2-naphthyl]methyl N,N-diphenylcarbamate IR (Nujol): 1700, 1600 cm$^{-1}$; NMR (DMSO-d$_6$, δ): 0.8–1.4 (2H, m), 1.7–2.1 (3H, m), 3.0 (1H, m), 4.06 (2H, s), 4.10 (1H, d, J=10.8 Hz), 4.20 (1H, d, J=10.8 Hz), 6.50 (1H, d, J=8 Hz), 6.71 (1H, d, J=8 Hz), 6.93 (1H, t, J=8 Hz), 7.2–7.6 (10H, m); FAB MS m/z: 466 (M$^+$+1)

(10) Sodium salt of [5-(carboxymethoxy)-2-fluoro-1,2,3,4-tetrahydro-2-naphthyl]methyl N,N-diphenylcarbamate IR (Nujol): 1700, 1600 cm$^{-1}$; NMR (DMSO-d$_6$, δ): 1.6–2.0 (2H, m), 2.5–3.0 (4H, m), 4.08 (2H, s), 4.25 (2H d, J=20 Hz), 6.47 (1H, d, J=8 Hz), 6.51 (1H, d, J=8 Hz), 6.97 (1H, d, J=8 Hz), 7.1–7.5 (10H, m); FAB MS m/z: 472 (M$^+$+1)

(11) Sodium salt of 2-[5-(carboxymethoxy)-1,2-methylene-1,2,3,4-tetrahydro-1-naphthyl]ethyl N,N-diphenylcarbamate IR (Nujol): 1705, 1600 cm$^{-1}$; NMR (DMSO-d$_6$, δ): 0.5–0.8 (2H, m), 1.0–2.0 (5H, m), 2.5–3.0 (2H, m), 4.05 (2H, s), 4.0–4.3 (2H, m), 6.49 (1H, d, J=8 Hz), 6.8–7.0 (2H, m), 7.1–7.5 (10H, m); FAB MS m/z: 480 (M$^+$+1)

(12) Sodium salt of 2-[5-(carboxymethoxy)-2-hydroxy-2-methyl-1,2,3,4-tetrahydro-1-naphthyl]ethyl N,N-diphenylcarbamate IR (Nujol): 3400, 1700, 1600 cm$^1$; NMR (DMSO-d$_6$, δ): 1.05 (3H, s), 1.1–2.0 (4H, m), 2.0–2.4 (2H, m), 2.75 (1H, m), 4.07 (2H, s), 4.0–4.3 (2H, m), 6.18 (1H, d, J=8 Hz), 6.46 (1H, d, J=8 Hz), 6.85 (1H, t, J=8 Hz), 7.1–7.5 (10H, m); FAB MS m/z: 498 (M$^+$+1)

(13) Sodium salt of 2-[5-(carboxymethoxy)-2-methyl-3,4-dihydro-1-naphthyl]ethyl N,N-diphenylcarbamate IR (Nujol): 1700, 1600 cm$^{-1}$; NMR (DMSO-d$_6$, δ): 1.68 (3H, s), 2.0–3.2 (4H, m), 3.2–4.2 (4H, m), 4.12 (2H, s), 6.5–6.7 (2H, m), 7.0–7.8 (11H, m); FAB MS m/z: 480 (M$^+$+1)

(14) Sodium salt of 2-[5-(carboxymethoxy)-1,2-dihydroxy-1,2,3,4-tetrahydro-1-naphthyl]ethyl N,N-diphenylcarbamate IR (Nujol): 3300, 1700, 1590 cm$^1$; NMR (DMSO-d$_6$, δ): 1.7–2.2 (4H, m), 2.5–2.7 (1H, m), 2.8–3.0(1H, m), 3.75 (1H, t, J=5.4 Hz), 4.0–4.3 (2H, m), 4.38 (2H, s), 6.6–6.8 (1H, m), 7.0–7.4 (12H, m); FAB MS m/z: 500 (M$^+$+1)

(15) Sodium salt of (cis)-2-[5-(carboxymethoxy)-2-hydroxy-1,2,3,4-tetrahydro-1-naphthyl]ethyl N,N-diphenylcarbamate IR (Nujol): 1700, 1600 cm$^{-1}$; NMR (DMSO-d$_6$, δ): 1.5–2.1 (4H, m), 2.4–2.8 (3H, m), 3.83 (1H, m), 4.06 (2H, s), 4.0–4.3 (2H, m), 6.29 (1H, d, J=8 Hz), 6.46 (1H, d, J=8 Hz), 6.87 (1H, t, J=8 Hz), 7.1–7.5 (10H, m); FAB MS m/z: 484 (M$^+$+1)

(16) Sodium salt of (trans)-2-[5-(carboxymethoxy)-2-hydroxy-1,2,3,4-tetrahydro-1-naphthyl]ethyl N,N-diphenylcarbamate IR (Nujol): 1700, 1600 cm$^{-1}$; NMR (DMSO-d$_6$, δ): 1.5–1.9 (4H, m), 2.5–2.7 (3H, m) 3.73 (1H, m), 4.06 (2H, s), 4.0–4.3 (2H, m), 6.39 (1H, d, J=8 Hz), 6.45 (1H, d, J=8 Hz), 6.87 (1H, t, J=8 Hz), 7.1–7.5 (10H, m); FAB MS m/z: 484 (M$^+$+1)

(17) Sodium salt of 2-[5-(carboxymethoxy)-2-fluoro-1,2,3,4-tetrahydro-1-naphthyl]ethyl N,N-diphenylcarbamate IR (Nujol): 1700, 1600 cm$^{-1}$; NMR (DMSO-d$_6$, δ): 1.5–2.0 (4H, m), 2.5–2.9 (3H, m), 3.73 (1H, m), 4.08 (2H, s), 4.0–4.3 (2H, m), 6.41 (1H, d, J=8 Hz), 6.49 (1H, d, J=8 Hz), 6.91 (1H, t, J=8 Hz), 7.1–7.5 (10H, m); FAB MS m/z: 486 (M$^+$+1)

(18) Sodium salt of 2-[5-(carboxymethoxy)-1-hydroxy-1,2,3,4-tetrahydro-1-naphthyl]ethyl N,N-diphenylcarbamate IR (Nujol): 3400, 1700, 1600 cm$^{-1}$; NMR (DMSO-d$_6$, δ): 1.4–2.0 (6H, m), 2.5–2.6 (2H, m), 4.0–4.2 (2H, m), 4.37 (2H, s), 6.58 (1H, t, J=5 Hz), 7.02 (2H, d, J=5 Hz), 7.1–7.5 (10H, m); FAB MS m/z: 484 (M$^+$+1)

(19) Sodium salt of 2-[5-(carboxymethoxy)-3,4-dihydro-1-naphthyl]ethyl N,N-diphenylcarbamate IR (Nujol): 1700, 1600 cm$^{-1}$; NMR (DMSO-d$_6$, δ): 2.0–2.2 (2H, m), 2.5–2.7 (4H, m), 4.0–4.3 (4H, m), 5.75 (1H, m), 6.63 (1H, d, J=8 Hz), 6.80 (1H, d, J=8 Hz), 6.98 (1H, t, J=8 Hz), 7.0–7.4 (10H, m); FAB MS m/z: 466 (M$^+$+1)

EXAMPLE 33

A solution of benzhydryl N-methyl-N-[[1,2,3,4-tetrahydro-5-(methoxycarbonylmethoxy)-2-naphthyl]methyl]carbamate (60 mg) in 0.1N sodium hydroxide (1.27 ml) and methanol was stirred at room temperature overnight and evaporated in vacuo. The residue was powdered from n-hexane to afford sodium salt of benzhydryl N-methyl-N-[[1,2,3,4-tetrahydro-5-(carboxymethoxy)-2-naphthyl]methyl]carbamate (50 mg) as a pale yellow powder.

mp: 100°–105° C.; IR (Nujol): 1695, 1605, 1200 cm$^1$; NMR (DMSO-d$_6$, δ): 1.2 (1H, br m), 1.75–2.05 (2H, m), 2.25–3.1 (4H, m), 2.87 and 3.08 (3H, s), 3.2–3.4 (2H, m), 4.06 (2H, s), 6.48 (2H, br d), 6.70 (1H, s), 6.94 (1H, br t), 7.2–7.4 (10H, m); FAB MS: 482 (M$^+$+1)

EXAMPLE 34

A solution of [1,2,3,4-tetrahydro-5-(methoxycarbonylmethoxy)-2-naphthyl]methyl N,N-diphenylcarbamate (600 mg) in 1N sodium hydroxide aqueous solution (2.0 ml), methanol (7 ml), and 1,2-dimethoxyethane (7 ml) was stirred at room temperature for 40 minutes, neutralized with 1N hydrochloric acid, evaporated in vacuo, and partitioned between ethyl acetate and water. The organic layer was washed with brine, dried over magnesium sulfate, and evaporated in vacuo. The residue was washed with n-hexane to afford a colorless powder (500 mg), which was dissolved in a mixture of ethanol (20 ml), methanol (30 ml) and tetrahydrofuran (10 ml). The solution was mixed with 1N sodium hydroxide aqueous solution (1.10 ml) and evaporated in vacuo. The residue was washed with n-hexane to afford sodium salt of [5-(carboxymethoxy)-1,2,3,4-tetrahydro-2-naphthyl]methyl N,N-diphenylcarbamate (475 mg) as a colorless powder.

IR (Nujol): 1715, 1625, 1600 (shoulder) cm$^{-1}$; MMR (DMSO-d$_6$, δ): 1.24 (1H, m), 1.83 (2H, m), 2.25–2.81 (4H, m), 4.03–4.08 (4H, m), 6.45–6.52 (2H, m), 6.92 (1H, t, J=7.8 Hz), 7.20–7.43 (10H, m); FAB MS m/z: 454 (M$^+$+1); Elemental Analysis Calcd. for C$_{26}$H$_{24}$NNaO$_5$: C 68.87, H 5.33, N 3.09; Found: C 68.59, H 5.31, N 3.08

EXAMPLE 35

A mixture of 1-[(3,4-dihydro-5-carboxymethoxy)-2-naphthyl)methyl]-5-diphenylmethyl-2(1H)-pyridone (100 mg) and a catalytic amount of 10% palladium on carbon (50% wet) were stirred at room temperature under atmospheric hydrogen gas for 5 hours. The catalyst was filtered off and the filtrate was evaporated in vacuo. The residue was purified by silica gel column chromatography (dichloromethane:methanol=5:1) to give 1-[(1,2,3,4-tetrahydro-5-carboxymethoxy-2-naphthyl)methyl]-5-diphenylmethyl-2(1H)-pyridone (94.5 mg) as a pale yellow powder.

mp: 162°–163° C.; IR (Nujol): 1670, 1610 cm$^{-1}$; NMR (DMSO-d$_6$, δ): 1.10–1.40 (1H, m), 1.70–4.00 (8H, m), 4.28 (2H, s), 5.39 (1H, s), 6.35–6.55 (4H, m), 6.90–7.00 (1H, m), 7.10–7.50 (11H, m); MASS (+APCI): 480 (M$^+$+1)

EXAMPLE 36

The following compound was obtained according to a similar manner to that of Example 35.

1-[(1,2,3,4-Tetrahydro-5-carboxymethoxy-2-naphthyl) methyl]-3-diphenylmethyl-2(1H)-pyridone mp: 185°–187° C.; IR (Nujol): 1730, 1640 cm$^{-1}$; NMR (DMSO-d$_6$, δ): 1.20–4.00 (9H, m), 4.30 (2H, s), 5.64 (1H, s), 6.15–6.25 (1H, m), 6.45–6.60 (2H, m), 6.70–7.40 (12H, m), 7.55–7.70 (1H, m)

EXAMPLE 37

Sodium salt of 2-[5-(carboxymethoxy)-2-methyl-1,2,3,4-tetrahydro-1-naphthyl]ethyl N,N-diphenylcarbamate was prepared from 2-[5-(ethoxycarbonylmethoxy)-2-methyl-3, 4-dihydro-1-naphthyl]ethyl N,N-diphenylcarbamate in a similar manner to that of Example 31.

IR (Nujol): 1700, 1600 cm$^{-1}$; NMR (DMSO-d$_6$, δ): 0.86 (3H, d, J=6.4 Hz), 1.3–2.9 (4H, m), 4.0–4.2 (4H, m), 6.33 (1H, d, J=8 Hz), 6.46 (1H, d, J=8 Hz), 6.87 (1H, t, J=8 Hz), 7.1–7.5 (10H, m); FAB MS m/z: 482 (M$^+$+1)

EXAMPLE 38

A solution of sodium salt (0.2 g) of (2R)-[5-(carboxymethoxy)-2-hydroxy-1,2,3,4-tetrahydro-2-naphthyl]methyl N,N-diphenylcarbamate in a mixture of water and ethyl acetate was washed with 1N-HCl solution and brine. The dried solvent was removed in vacuo and the residue was recrystallized from ethyl ether to give (2R)-[5-(carboxymethoxy)-2-hydroxy-1,2,3,4-tetrahydro-2-naphthyl]methyl N,N-diphenylcarbamate (150 mg).

NMR (CDCl$_3$, δ): 1.6–2.0 (2H, m), 2.6–3.0 (4H, m), 4.15 (2H, s), 4.64 (2H, s), 6.54 (1H, d, J=8Hz), 6.69 (1H, d, J=8Hz), 7.07 (1H, t, J=8Hz), 7.1–7.5 (10H, m)

We claim:
1. A compound of the formula:

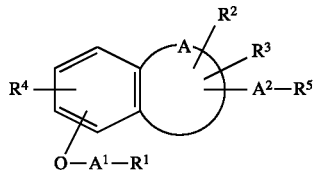

wherein R$^1$ is carboxy or protected carboxy,
R$^2$ is hydrogen, hydroxy or protected hydroxy,
R$^3$ is hydrogen, hydroxy, protected hydroxy, lower alkyl or halogen,
R$^4$ is hydrogen or halogen,
A$^1$ is lower alkylene,
A$^2$ is bond or lower alkylene, —R$^5$ is

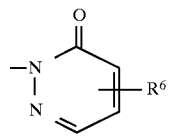

in which R$^6$ is mono (or di or tri)aryl(lower) alkyl, and

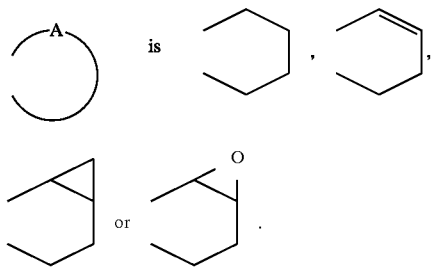

and a pharmaceutically acceptable salt thereof.
2. A compound of claim 1, wherein
R$^1$ is carboxy or esterified carboxy,
A$^1$ is C$_1$–C$_3$ alkylene,
A$^2$ is a bond or C$_1$–C$_3$ alkylene, and
—R$^5$ is

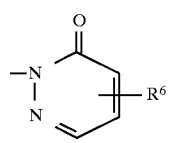

in which R$^6$ is diaryl(lower)alkyl.
3. A compound of claim 2, wherein
R$^1$ is carboxy or lower alkoxycarbonyl,
R$^2$ is hydrogen, hydroxy or acyloxy,
R$^3$ is hydrogen, hydroxy, acyloxy, lower alkyl or halogen,
R$^4$ is hydrogen or halogen,
A$^1$ is methylene,
A$^2$ is a bond, methylene or ethylene, and
—R$^5$ is

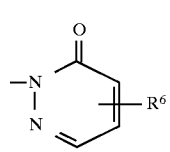

in which R$^6$ is diphenylmethyl.
4. A compound of claim 3, which is a compound of the formula:

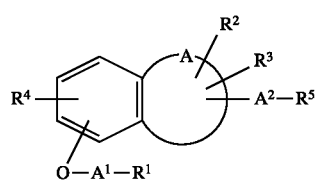

wherein R$^1$ is carboxy or lower alkoxycarbonyl, $R^2$ is hydrogen or hydroxy,
$R^3$ is hydrogen, hydroxy, lower alkyl or halogen,
$R^4$ is hydrogen or halogen,
$A^1$ is methylene,
$A^2$ is methylene or ethylene, and —$R^5$ is 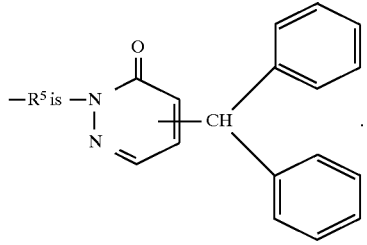.

5. A compound of claim 4, which is (S)-2-[(1,2,3,4-tetrahydro-5-carboxymethoxy-2-naphthyl)methyl]-6-diphenylmethyl-3(2H)-pyridazinone.

6. A process for preparing a compound of the formula:

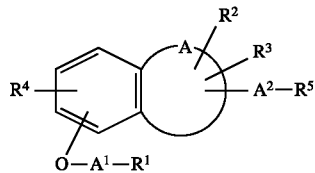

wherein $R^1$ is carboxy or protected carboxy,
$R^2$ is hydrogen, hydroxy or protected hydroxy,
$R^3$ is hydrogen, hydroxy, protected hydroxy, lower alkyl or halogen,
$R^4$ is hydrogen or halogen,
$A^1$ is lower alkylene,
$A^2$ is bond or lower alkylene,
—$R^5$ is

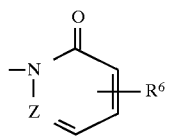

in which $R^6$ is mono (or di or tri)aryl(lower)alkyl, and

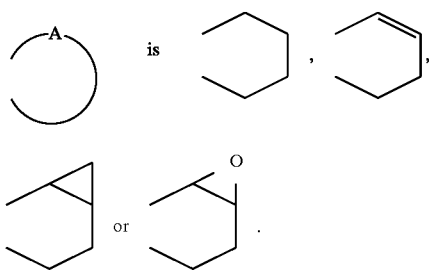

or a salt thereof,
which comprises (1) reacting a compound of the formula:

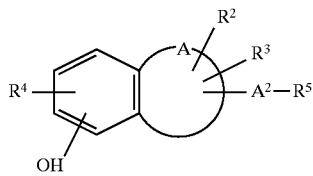

wherein $R^2$, $R^3$, $R^4$, $R^5$, $A^1$, $A^2$ and

are each as defined above,
or a salt thereof with a compound of the formula:

$X^1$—$A^1$—$R^1$ wherein $R^1$ and $A^1$ are each as defined above, and $X^1$ is acid residue,
or a salt thereof to give a compound of the formula:

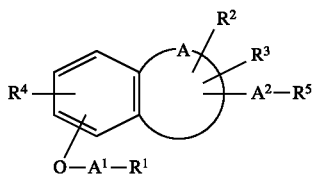

wherein $R^1$, $R^2$, $R^3$, $R^4$, $R^5$, $A^1$, $A^2$ and

are each as defined above,
or a salt thereof, or
(2) subjecting a compound of the formula:

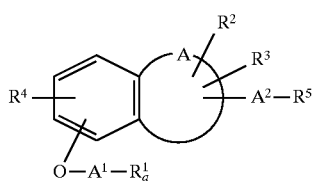

wherein $R^2$, $R^3$, $R^4$, $R^5$, $A^1$, $A^2$ and

are each as defined above, and
$R^1_a$ is protected carboxy,
or a salt thereof to elimination reaction of the carboxy protective group to give a compound of the formula:

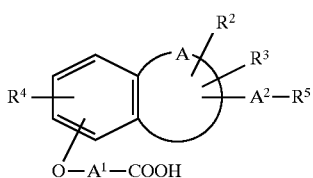

wherein $R^2$, $R^3$, $R^4$, $R^5$, $A^1$, $A^2$ and

are each as defined above,
or a salt thereof.

7. A pharmaceutical composition which comprises, as an active ingredient, a compound of claim 1 or a pharmaceutically acceptable salt thereof in admixture with a pharmaceutically acceptable carrier.

8. A method for treating of preventing arterial obstruction, restenosis after percutaneous transluminal coronary angioplasty, arteriosclerosis, cerebrovascular disease or ischemic heart disease which comprises administering an effective amount of the compound of claim 1 or a pharmaceutically acceptable salt thereof to a human or animal.

9. A process for preparing a pharmaceutical composition which comprises admixing a compound of claim 1 or a pharmaceutically acceptable salt thereof with a pharmaceutically acceptable carrier.

10. A method for agonising prostaglandin $I_2$ activity, which comprises administering an effective amount of the compound of claim 1 or pharmaceutical acceptable salts thereof to a human or animal.

11. A method for inhibiting platelet aggregation, which comprises administering an effective amount of the compound of claim 1 or pharmaceutical acceptable salts thereof to a human or animal.

12. A method for suppressing blood pressure, which comprises administering an effective amount of the compound of claim 1 or pharmaceutical acceptable salts thereof to a human or animal.

* * * * *